(12) United States Patent
Levin et al.

(10) Patent No.: US 8,280,640 B2
(45) Date of Patent: Oct. 2, 2012

(54) SYSTEM AND METHOD FOR PATTERN RECOGNITION IN SEQUENTIAL DATA

(75) Inventors: Eugene Levin, Kailua-Kona, HI (US); Martha Elizabeth Corey, San Francisco, CA (US)

(73) Assignee: Eloret Corporation, Sunnyvale, CA (US)

( * ) Notice: Subject to any disclaimer, the term of this patent is extended or adjusted under 35 U.S.C. 154(b) by 914 days.

(21) Appl. No.: 10/916,370

(22) Filed: Aug. 11, 2004

(65) Prior Publication Data

US 2005/0187916 A1  Aug. 25, 2005

Related U.S. Application Data

(60) Provisional application No. 60/493,766, filed on Aug. 11, 2003.

(51) Int. Cl.
*G01N 33/50* (2006.01)
*G01N 33/48* (2006.01)

(52) U.S. Cl. ............................................. 702/19; 702/20
(58) Field of Classification Search .................. None
See application file for complete search history.

(56) References Cited

U.S. PATENT DOCUMENTS

| | | | | |
|---|---|---|---|---|
| 3,702,392 A | * | 11/1972 | St. Jean | 235/380 |
| 5,701,256 A | * | 12/1997 | Marr et al. | 702/20 |
| 6,785,677 B1 | | 8/2004 | Fritchman | 707/6 |
| 2005/0089930 A1 | * | 4/2005 | Schneider et al. | 435/7.1 |

OTHER PUBLICATIONS

Sugiyama et al., "Identification of Transmembrane Protein Functions by Binary Topology Patterns", *Protein Engineering*, 16(7):479-488 (2003).
Altschul et al., "Basic Local Alignment Search Tool", *J. Mol. Biol.*, 1990, 215:403-410.
Atal, "Automatic Recognition of Speakers from Their Voices", *Proceedings of the IEEE*, Apr. 1976, 64(4):460-475.
Burkhardt et al., "q-gram Based Database Searching Using a Suffix Array (QUASAR)", *3rd Ann. International Conference on Computational Molecular Biology*, Lyon, Apr. 11-14, 1999.
Delcher et al., "Alignment of whole genomes", *Nucleic Acids Research*, 1999, 27(11):2369-2376.
Kurtz et al., "REPuter: Fast Computation of Maximal Repeats in Complete Genomes", 1999, 15(5):426-427.
Myers, "A Fast Bit-Vector Algorithm for Approximate String Matching Based on Dynamic Programming", *Journal of the ACM*, May 1999, 45(3):395-415.

* cited by examiner

*Primary Examiner* — Jason Sims
(74) *Attorney, Agent, or Firm* — James Farmer; Van Cott, Bagley, Cornwall & McCarthy

(57) ABSTRACT

The present invention is based on the encoding of sequential data or sequences in a novel manner that permits efficient storage and processing of sequential data, as well as methods for searching sequences or databases of sequences. The methods and systems of the current invention may be adapted broadly to various fields of application and to a variety of sequences types. For example, the current invention has broad application including to the fields of bioinformatics, molecular biology, pharmacogenomics, phonetic sequences, lexicographic sequences, signal analysis, game playing, law enforcement, biometrics, medical diagnosis, equipment maintenance and micro-array data analysis.

18 Claims, 1 Drawing Sheet

Step 1: Generate the symbol-feature map and associated statistics i. Given a large representative population of sequences, identify the features of interest that are associated with some, but not all, of the symbols, sets of symbols or patterns of symbols that appear in the sequences.
ii. Develop a symbol-feature map that associates a symbol, a set of symbols or a pattern of symbols with a given feature.
iii. Generate a *frequency count* of the symbol-feature combinations found in the population.
iv. Quantify the *substitution likelihood* by counting the number of times similar sequences have a symbol with a given feature replaced by another symbol without that feature.
v. Normalize the substitution likelihood using the frequency count to get a substitution score for each feature-to-feature, nonfeature-to-nonfeature and feature-to-nonfeature alignment.

Step 2: Create and store the sieves i. Given the symbol-feature map developed in step 1.ii, process a given set of sequences into a set of sieves so as to generate a plurality of bit-vectors associated with each sequence, where each bit-vector is associated with a specific and meaningful feature.
ii. Store the sieves.

Step 3: Given a probe sieve P, find a set of similar sieves

For each candidate sieve drawn from the set of stored sieves,
    For each feature-vector in the probe's sieve,
        i. Align the probe feature-vector with the corresponding candidate vector. Score using the substitution scores generated in Step 1.v.
        ii. If the alignment score falls below a given threshold, stop processing the sieve and impute dissimilarity.
        iii. If processing successfully completes for all the bit-vectors in the sieve, impute similarity.

Step 4: Order the set of similar sieves for viewing

For each similar sieve found in Step 3, order and present the sieves based on their final scores.

SYSTEM AND METHOD FOR PATTERN RECOGNITION IN SEQUENTIAL DATA

CROSS REFERENCE TO RELATED APPLICATION(S)

This application claims the benefit of priority under 35 U.S.C. §119(e) of U.S. Ser. No. 60/493,766, filed Aug. 11, 2003, the entire content of which is incorporated herein by reference.

BACKGROUND OF THE INVENTION

1. Field of the Invention

The invention relates generally to systems and methods of efficiently searching for desired patterns in sequential data and more specifically to sequential data with broad application to a variety of fields, including but not limited to bioinformatics, molecular biology, pharmacogenomics, phonetic sequences, lexicographic sequences, signal analysis, game playing, law enforcement, biometrics, medical diagnosis, equipment maintenance, and micro-array data analysis.

2. Background Information

Exact and approximate string matching are two of the main techniques used in applications such as text searching, computational biology or bioinformatics, and pattern recognition.

A natural extension includes multi-pattern searching, or searching for several patterns simultaneously in order to report all occurrences with a limited number of differences. Similarly the method may be extended to multi-modal pattern detection that includes searching several different data bases with a set of patterns each of which is appropriate to the particular data base. This has several applications including biometrics, virus and intrusion detection, spelling applications, text retrieval under synonym or thesaurus expansion, several problems in computational biology, and batch processing of single-pattern approximate searching.

The field of bioinformatics includes the systematic development and application of information technologies and data processing techniques for collecting, searching, analyzing and displaying data obtained by experiments to make observations concerning biological processes. Bioinformatics is concerned with the use of computing in biological research areas such as genomics, transcriptomics, proteomics, genetics and evolution (see, for example, Goodman, Current Opinion in Biotechnology, 2002, 13:1:68-71).

High-throughput sequencing projects have generated complete genome sequences for scores of microbes and several eukaryotes, including human. Successful achievement of genome projects have yielded complete genomic sequences of several species, including *H. sapiens, C. elegans, A. thaliana, D. melanogaster, M. musculus, S. pombe, S. cerevisiae*, rice, dozens of prokaryote genomes, and hundreds of virus genomes (the initial sequences of the human genome, for example, may be found at the following references: International Human Genome Sequencing Consortium, Initial sequencing and analysis of the human genome, Nature 409, pp. 860-921, 2001, and J. C. Venter et al., The sequence of the human genome, Science 291, p. 1304, 2001).

With this explosive growth of biological sequence data, biological information is less frequently published in the conventional way via a publication in a scientific journal, but instead deposited into a database. In the last two decades these databases have become essential tools for researchers in biological sciences. Such databases are generally classified according to the type of sequence information they contain. Basic types of sequence-related databases include nucleic acid sequences, amino acid sequences representing polypeptide primary structures, and protein tertiary structures, as well as various specialized data collections.

Biologists use these comprehensive data in their attempts to discover the biological functions of genes and the proteins they encode. For many proteins, for example, it is possible to make inferences of function based simply on recognizable similarity with previously characterized sequences. Currently, between one-third and one-half of the genes in newly sequenced genomes can be annotated on the basis of recognized similarity to genes of other organisms. Furthermore, as more genes are characterized, a greater fraction of new and extant genomes can be annotated through similarity searches.

The ability to make valid inferences based on sequence similarity depends on the relationship between sequence, structure and function—all of which revolve around the imputation of common ancestral roots or homology.

Given this basis for sequence similarity, divergence between homologous sequences shows a consistent rate pattern based on the nature of evolution. Protein function mutates and evolves more slowly than protein structure and protein structure evolves more slowly than gene and amino acid sequences.

While the usual method for detecting homology is sequence comparison, effective annotation of unknown genes requires that we have some ability to determine functional similarities. While finding sequence similarity is meaningful, finding structural similarity brings us closer to our aim, which is the accurate determination of a genetic function. Given a similarity-finding technique that provides sufficient clues about structure—and thereby function—we can use those clues to suggest experiments, form hypotheses, and thereby pursue further characterization of unknown proteins.

Because similarity-finding has such a central role in annotating existing and newly sequenced genomes, many methods have been developed including the following:

BLAST (Basic Local Alignment Search Tool) described by S. F. Altschul, W. Gish, W. Miller, E. Myers and D. J. Lipman, Basic local alignment search tool, J. Mol. Biol., 215, 403-410 (1990); and the family of related tools that it spawned, including WU-Blast, Psi-Blast, MegaBlast and BL2SEQ;

SENSEI; see a description by D. States on the SENSEI world site at the hypertext transfer protocol "stateslab.wustl.edu/software/sensei/";

MUMmer; see A. L. Delcher, S. Kasif, R. D. Fleischmann, J. Peterson, O. White, and S. L. Salzberg, Alignment of whole genomes, Nucleic Acids Research, 27:11, 2369-2376 (1999);

QUASAR; see S. Burkhardt, A. Crauser, H—P. Lenhof, E. Rivals, P. Ferragina and M. Vingron, q-gra based database searching using a suffix array, 3rd Ann. International Conference on Computational Molecular Biology, Lyon Apr. 11-14, 1999; and REPuter; see S. Kurtz and C. Schleiermacher, REPuter—Fast computation of maximal repeats in complete genomes; Bioinformatics, 15:5, 426-427 (1999).

In addition to the field of bioinformatics, sequential data is becoming increasingly voluminous in other disciplines, thereby requiring efficient methods and systems for processing the data. One such example is the area of personal identification by biometric data (for example, fingerprints, hand geometry, iris, retina, signature, voiceprint, facial thermogram, hand vein, gait, ear, odor, keystroke dynamics, etc.). Homeland Security, electronic banking, e-commerce and smartcards, along with increased emphasis on the privacy and security of information stored in various databases, lead to the generation of massive amounts of sequence data as well as a need for automatic personal identification using biometric data. Accurate automatic identification is needed in applications involving the use of passports, cellular telephones, automatic teller machines and driver licenses.

The existing search tools for searching and processing sequential data, including in the fields of bioinformatics and biometrics, are, however, limited in application due to lengthy processing times and/or lack of sensitivity. Therefore, there is a need for improved systems and methods for efficiently and accurately storing, processing, and searching large amounts of sequential data.

SUMMARY OF THE INVENTION

An efficient process is described for searching sequences, including comparison with a query sequence representing a pattern of interest in order to locate exact or close matches between sequences. The method has broad application including, but not limited to, sequences arising in bioinformatics, phonetic sequences, signal analysis, image patterns, lexicographic sequences, biometrics, medical diagnosis, game playing and equipment maintenance.

The present invention is based on the decomposition of the information content of a sequence into a set of simpler representations including a set of at least two binary strings. For each binary string of a target sequence set, a match with the corresponding binary string of the query pattern represents a condition identifying a candidate match. Thus each of the binary strings serves to act as a sieve or filter to narrow the search space, or alternately to decompose the search space into a set of simpler subspaces. A true match is confirmed where the set of all binary strings representing the target sequence form a match (matches) with the corresponding binary strings of the query sequence and that the match (matches) occur in the same index position (positions) of the sequences.

This decomposition enables the search process to make maximum use of bit-level computational and logical steps which are inherent operations of digital processors and can be implemented at the level of machine language. It also facilitates the use of parallel processors or clusters of small computers. Although the method can be carried out using any general-purpose digital computer it is suggested that an accelerator chip or special processing module (e.g. Programmable Field Array) for the particular operations needed by the method would result in further speed improvement.

The systems and methods of the invention may be adapted to any of the very large number of existing specialized search, alignment and pattern recognition techniques and codes. One advantage is faster processing with the speed advantage becoming most evident when the query and/or target sequences are very long and a match is rare rather than common. The advantage is also most evident when the search algorithm is complex and time consuming such as affine Smith-Waterman, Hidden Markov Model or Neural Net methods.

Another advantage is greater sensitivity (fewer false matches) for searches that seek 'best' approximate matches in accordance with some user-selected mismatch scoring criterion. This advantage is due to the flexibility to perform the decomposition of the query and target sequences in a manner that emphasizes the most significant features of the desired search such as the biochemical properties of amino acids, for example.

In one embodiment, the present invention relates to methods of comparing sequential data including providing a target sequence and a query sequence, where each sequence is encoded as a set of at least two n-bit binary strings. Furthermore, each bit of each binary string of a sequence is aligned with the corresponding bit of the other binary string, thereby identifying n groups of aligned bits, where each group of aligned bits defines an identity of a component of a sequence. The methods further include determining, by an ordered comparison of the binary strings of the query sequence with the corresponding binary strings of the sequences of the database, an exact or partial match between the query sequence and the sequence of the database, and generating an indication of a match of the target and query sequences based on the ordered comparison.

In another embodiment, the present invention includes a computer system having a searchable database of sequences, where each sequence is encoded as a set of at least two n-bit binary strings, each bit of each binary string is aligned with the corresponding bit of the other binary string, thereby identifying n groups of aligned bits, and where each group of aligned bits defines an identity of a component of the sequence. Such a computer system further includes a user interface capable of receiving a selection of at least two sequences for determining, by an ordered comparison of corresponding binary strings of the selected sequences, a match between the selected sequences, and displaying the results of the determination.

In yet another embodiment, the current invention includes a computer-readable data storage medium having a plurality of digitally-encoded sequences. Each of the digitally-encoded sequences are encoded as a set of at least two n-bit binary strings, where each bit of each binary string is aligned with the corresponding bit of the other binary string, thereby identifying n groups of aligned bits, and each group of aligned bits defines an identity of a component of the sequence.

According to the present invention, a binary string includes a plurality of binary string components. Binary strings encoding a sequence may be aligned in parallel, for example, in order to determine the encoded sequence components. The identity of a sequence component is therefore defined by a combination of aligned binary string components at a given index location. Furthermore, in one embodiment of the invention, a combination of less then the entirety of binary string components at an index location defines an aspect of a sequence component.

In one embodiment, the length of the query sequence may be different from the length of the target sequence. A comparison of a sequences not of identical length may include a tandem extension of the shorter sequence followed by one bit shifts in the alignment of the sequences subject to comparison.

Corresponding binary strings, and, therefore, sequences encoded as a set of at least two binary strings, may be compared in a manner consistent with a logical computer operation. For example, a comparison of corresponding binary strings may include a bit-logical summation. In another embodiment, a comparison may include a numerical subtraction of two corresponding binary strings. In yet another embodiment, a comparison may include forming a plurality of comparison matrices, each matrix having corresponding binary strings for each pair of corresponding binary strings, and combining the matrices using a logical operation capable of identifying common regions or regions common to each sequence being compared. One example of such a matrix is a 'Dotlet matrix' as further described below.

A comparison of sequences according to the present invention may identify a variety of matches. In one embodiment, a match may include an exact match, between the sequences subject to comparison, of sequence components. A match may further include a partial match of sequence components or a match in less then the entirety of sequence components being compared. In another embodiment, a comparison is capable of identifying mismatching sequence components. In some instances, criteria for a match may be selected, by a user, for example, prior to the ordered comparison and, in some instances, the results of the comparison may be displayed according to the criteria selected prior to the ordered comparison. In one embodiment, the comparison may allow for the introduction of gaps into one or more of the sequences being compared. The inventive methods further include displaying the results of the comparison. The displaying may occur, for example, on a user interface or a graphic interface, such as a monitor or computer monitor.

In one embodiment, the sequences of the invention include nucleic acid sequences or nucleotide sequences. Nucleotide sequences of the inventive methods each may be encoded, for example, as a set of at least two binary strings. In one embodiment of the invention, nucleotide sequences of the database may each be associated with a particular phenotype or characteristic. An example of such a phenotype or characteristic may include an indication of at least one drug metabolism characteristic. In such an embodiment, the results of a comparison of sequences may include a prediction of at least one drug metabolism characteristic associated with the query sequence. A method may further include selecting a drug therapy or regimen based on the results of such a comparison. The present invention further includes methods of comparing at least two gene expression profiles.

In another embodiment, the sequences of the invention may include peptide or amino acid sequences. In such an embodiment, each sequence may be encoded as a set of at least five binary strings. For some applications, the encoding as five binary strings is appropriate to capture the desired features of the search, for example, to locate structural characteristics of the protein resulting from the amino acid sequence. For other applications it is convenient to encode amino acid sequences as a set of six binary strings, for example, by using the corresponding codon triplet in order to compare amino acid and nucleic acid sequences. The method may further include scoring mismatching amino acids of the compared sequences based on the identities of the amino acids aligned in the comparison. Scoring mismatching amino acids may include, for example, using a scoring matrix such as PAM or BLOSUM. The method further permits flexibility to construct scoring criteria selected to emphasize or weight the characteristics of the pattern deemed to be most important by the user.

In one embodiment, sequences of the invention may comprise lexicographic sequences.

In yet another embodiment, sequences of the invention may comprise phonetic sequences. In such an instance, each sequence component includes a phoneme. In another embodiment, the sequences comprise speech pattern sequences. Such speech pattern sequences may include duration, frequency or intonation speech data. A speech pattern sequence also may include formant pattern data. Speech pattern sequences, such as those sequences in a database, may each be associated with a particular speaker. In such an instance, a comparison of sequences may allow for the identification of a speaker.

In another embodiment, sequences of the invention may include signal analysis sequences. Signal analysis sequences may include electromagnetic data, optical data, acoustic data, or seismic data sequences. Where signal analysis sequences include seismic data sequences, certain seismic data sequences, such as those in a database, may be associated with an earthquake activity profile or the presence of an oil-bearing subsurface dome structure As such, the results of a comparison of such sequences may include a prediction of earthquake activity or the location of promising oil deposits. Additionally, seismic data sequences, such as those in a database, may each be associated with a particular volcanic activity profile, and the results of a comparison of such sequences may include a prediction of volcanic activity. In another instance, signal analysis sequences may be radar data sequences. In yet another instance, signal analysis sequences may include sonar data sequences. In an instance where signal analysis sequences include continuous sequence data, the continuous sequence data may be divided into discrete subsets prior to encoding the signal analysis sequences each as a set of multiple binary strings.

In yet another embodiment of the invention, sequences may include data derived from a graphic image. A graphic image may include an x-ray image, CAT scan image, or a Magnetic Resonance Image (MRI image). Such graphic images may be represented as sequences by means of scanning techniques and sequences stored in a database may be associated with a particular medical condition or medical diagnosis. In such an instance, a comparison of sequences may produce a prediction of a medical condition or diagnosis. In another example, a graphic image may include a television image. In such a case, the data of a graphic image may include pixel location data. In another example, a graphic image may include a fingerprint image. In such a case, the graphical image may include locations of specific features (minutia) such as ridge terminations or ridge bifurcations that are used to match fingerprints. In yet anther example, a graphic image may include a photographic image.

In another embodiment, sequences of the invention may include sequential data derived from an interactive game. Data derived from an interactive game may include, for example, a series of executable moves or steps, or a state of at least one executable element. In such an embodiment the results of a comparison of sequences may include a prediction of a game outcome. A variety of interactive games are herein envisioned. One such interactive game includes chess.

In yet another embodiment, sequences of the invention may include law enforcement related sequence data useful in solving a crime or identifying an individual to enhance homeland security. Law enforcement related sequence data may include, for example, fingerprint data, voiceprint data, or genetic profile data. Accordingly, a sequence, such as a sequence in a database, may be associated with the identity of a subject or individual, and the results of a comparison of sequences may include a prediction of a subject's identity. The method may be used for multi-modal pattern recognition wherein the overall scoring of an approximate match is based on partial scores from various sequences and patterns of dissimilar type. Thus, for example, combining information from both fingerprint data and voiceprint data.

In another embodiment, sequences of the invention may include sequence data related to the status of mechanical equipment. Status may include, for example, temperature, pressure, strains, or the level readings of gauges. Such sequence data may include a series of measurements recorded at regular time intervals and serve as a pattern to compare with stored sequences that are known indicators of the need for maintenance or of impending failure.

The present invention further includes methods of identifying matching biomolecule sequence data. Such methods include providing a searchable database of sequences, the database including a target biomolecule sequence and a query biomolecule sequence. Each sequence may be encoded as a set of at least two n-bit binary strings where each bit of each binary string is aligned with the corresponding bit of the other binary string, thereby identifying n groups of aligned bits, where each group of aligned bits defines an identity of a component of the sequence. The methods further include determining, by an ordered comparison of the binary strings of the query biomolecule sequence with corresponding binary strings of the target biomolecule sequence, a match between the query target sequence and the target biomolecule sequence. The method extends to approximate matches where scores are assigned to both exact matches and mismatches in accordance with a scoring table and the results return the highest scoring approximate matches.

The current invention further includes methods of identifying a region of interest in a sequence. The methods include providing a query sequence representing a region of interest and a target sequence, where each sequence is encoded as a set of at least two n-bit binary strings, where each bit of each binary string is aligned with the corresponding bit of the other binary string, thereby identifying n groups of aligned bits, and where each group of aligned bits defines an identity of a component of the sequence. The methods further include determining, by an ordered comparison of the binary strings of the query sequence with corresponding binary strings of the target sequence, a match between the query sequence and a region of the target sequence, thereby identifying a region of interest in the target sequence, for example a motif. The methods may further include generating an indication of a match of the target sequence and a region of the query sequence based on the ordered comparison.

Various types of sequence data are useful in the current methods of identifying a region of interest in a sequence. Sequences may include, for example, nucleotide sequences, amino acid sequences, phonetic sequences, speech pattern sequences signal analysis sequences, sequence data derived from a graphic image, data derived from an interactive game, or law enforcement related sequence data.

In another embodiment of the current methods of identifying a region of interest in a sequence, the sequences may include amino acid sequences. Various query sequences representing a region of interest in an amino acid sequence are encompassed by the present methods and may be categorized as specific amino acid regions commonly recognized, but may be any region selected by a user.

The methods include providing a subject expression profile of a sample from a subject, where the subject expression profile is encoded as a set of at least two binary strings, and providing a plurality of reference profiles, each reference profile similarly encoded as a set of at least two binary strings, where the subject expression profile and each reference profile has a plurality of values, each value representing the expression level of a gene. The method further includes comparing, by an ordered comparison of the binary strings of the subject expression profile sequence with the corresponding binary strings of at least one reference profile sequence, the reference profile and the subject expression profile.

BRIEF DESCRIPTION OF THE DRAWINGS

FIG. 1 is a flow chart illustrating a method according to an embodiment of the invention.

DETAILED DESCRIPTION OF THE INVENTION

An efficient process is described for searching sequences, including comparison with a query sequence representing a pattern of interest in order to locate exact or close matches between sequences. The method has broad application including, but not limited to, sequences arising in bioinformatics, phonetic sequences, signal analysis, image patterns, lexicographic sequences, biometrics, medical diagnosis, game playing and equipment maintenance.

The present invention is based on the decomposition of the information content of a sequence into a set of simpler representations including a set of at least two binary strings. For each binary string of a target sequence set, a match with the corresponding binary string of the query pattern represents a condition identifying a candidate match. Thus each of the binary strings serves to act as a sieve or filter to narrow the search space, or alternately to decompose the search space into a set of simpler subspaces. A true match is confirmed where the set of all binary strings representing the target sequence form a match (matches) with the corresponding binary strings of the query sequence and that the match (matches) occur in the same index position (positions) of the sequences.

This decomposition enables the search process to make maximum use of bit-level computational and logical steps which are inherent operations of digital processors and can be implemented at the level of machine language. It also facilitates the use of parallel processors or clusters of small computers. Although the method can be carried out using any general-purpose digital computer it is suggested that an accelerator chip or special processing module (e.g. Programmable Field Array) for the particular operations needed by the method would result in further speed improvement.

The systems and methods of the invention may be adapted to any of the very large number of existing specialized search, alignment and pattern recognition techniques and codes. One advantage is faster processing with the speed advantage becoming most evident when the query and/or target sequences are very long and a match is rare rather than common. The advantage is also most evident when the search algorithm is complex and time consuming such as affine Smith-Waterman, Hidden Markov Model or Neural Net methods.

Another advantage is greater sensitivity (fewer false matches) for searches that seek 'best' approximate matches in accordance with some user-selected mismatch scoring criterion. This advantage is due to the flexibility to perform the decomposition of the query and target sequences in a manner that emphasizes the most significant features of the desired search such as the biochemical properties of amino acids for example.

It is understood that this invention is not limited to the particular methodology, protocols, and systems described, as these may vary while maintaining the essences of the invention. It is also to be understood that the terminology used herein is for the purpose of describing particular embodiments only, and is not intended to limit the scope of the present invention which will be described by the appended claims.

It must be noted that as used herein and in the appended claims, the singular forms "a", "an", and "the" include plural reference unless the context clearly dictates otherwise. Thus, for example, reference to a "sequence" includes a plurality of such sequences, reference to a "nucleotide" sequence" includes one or more nucleotide sequences and equivalents thereof known to those skilled in the art.

Unless defined otherwise, all technical and scientific terms used herein have the same meanings as commonly understood by one of ordinary skill in the art to which this invention belongs. Although any methods and systems similar or equivalent to those described herein can be used in the practice or testing of the present invention, the methods, devices, and materials are now described. All publications mentioned herein are incorporated herein by reference for the purpose of describing and disclosing the processes, systems and methodologies which are reported in the publications which might be used in connection with the invention. Nothing herein is to be construed as an admission that applicants are not entitled to antedate such disclosure.

The methods and systems of the current invention may be adapted broadly to various fields of application and to a variety of sequence types. For example, the current invention has broad application including, without limitation, to the fields of bioinformatics, molecular biology, pharmacogenomics, phonetic sequences, lexicographic sequences, signal analysis, game playing, law enforcement, biometrics, medical diagnosis, equipment maintenance and micro-array data analysis.

The current invention relates to sequential data, where individual sequences are encoded as a set of at least two binary strings. According to the present invention, a binary string includes a plurality of binary string components. Each sequence is encoded as a set of at least two n-bit binary strings. The number of bits in a binary string (n) is equal to the number of components of the corresponding sequence represented by the encoding. Each bit of each binary string is aligned with the corresponding bit of the other binary string and, thereby, identifies groups of aligned bits, and each group of aligned bits defines an identity of a component of the sequence. For example, the identity of a sequence component may be defined by a combination of aligned binary strings at given index location. Furthermore, a combination of less then the entirety of binary string components at an index location may define an aspect of a sequence component, even if the identity of the sequence component is not apparent from the combination of less then the entirety of binary string components. For example, if an amino acid sequence is encoded so as to represent the structure-inducing characteristics, the entire binary string set for a particular member of the sequence might uniquely define a particular amino acid whereas a partial set of the binary strings might indicate one of several amino acids that tend to create the formation of an alpha helix. Similarly, if the encoding of an amino acid sequence was selected to represent the biochemical properties of the amino acids, the complete set of binary strings at a specific index location would again define a unique amino acid whereas a partial set might only indicate that the amino acid was one of the amino acids that contained a hydrophilic side chain. In general, the encoding has the property that the complete set of binary strings at a given index location results in a unique identification of the member of the sequence, whereas a partial set results in a subspace containing members related in accordance with the specific choice of binary encoding.

The present invention may be implemented using hardware, software or a combination thereof and may be implemented in a computer system or other processing system. In one embodiment, the invention is directed to a computer system capable of carrying out the functionality described herein. For example, the present invention may include a computer system having a searchable database of sequences, where each sequence is similarly encoded as a set of at least two binary strings. Such a computer system further includes a user interface capable of receiving a selection of at least two sequences for determining, by an ordered comparison of corresponding binary strings of the selected sequences, a match between the selected sequences, and displaying the results of the determination.

An example computer system includes one or more processors, such as a processor connected to a communication bus. A computer system may also include a main memory, preferably random access memory (RAM), and can also include a secondary memory. The secondary memory can include, for example, a hard disk drive and/or a removable storage drive, including a floppy disk drive, a magnetic tape drive, an optical disk drive, etc. which is read by and written to by the removable storage drive. As will be appreciated by those skilled in the art, a removable storage unit includes a computer usable storage medium having stored therein computer software and/or data. Further, it will be appreciated by one of ordinary skill in the art that a computer can be part of a larger system. For example, a computer can be a server computer that is in data communication with other computers.

A computer system can also include a communications interface that allows software and data to be transferred between the computer system and external devices. Examples of communications interface can include a modem, a network interface (such as an Ethernet card), a communications port, a PCMCIA slot and card, a wireless connection, etc. Software and data transferred via a communications interface are in the form of signals which can be electronic, electromagnetic, optical or other form of signal capable of being received by the communications interface. These signals may be provided to the communications interface via a channel, which carries signals and can be implemented using wire or cable, fiber optics, a phone line, and other communications channels.

The terms "electronic storage medium" and "computer-readable data storage medium" are used herein to generally refer to electronic media such as a removable storage device, a hard disk installed in a hard disk drive and signals. These computer program products are means for providing software to the computer system. In one embodiment, the current invention includes a computer-readable storage medium having a plurality of digitally-encoded sequences, where each sequence is similarly encoded as a set of at least two binary strings.

Computer programs which represent controllers of the computer system may be stored in the main memory and/or secondary memory of the computer. Computer programs can also be received via a communications interface. Such computer programs, when executed, enable the computer system to perform the features of the present invention as disclosed herein. In particular, the computer programs, when executed, enable the processor to perform the features of the present invention. Where the invention is implemented using software, the software may be stored in a computer program product and loaded into the computer system using a removable storage drive, hard drive, or communications interface. The software, when executed by the processor, causes the processor to perform the functions of the invention as described herein.

In another embodiment, the invention is implemented primarily in hardware using, for example, hardware components such as Field Programmable Gate Arrays (FPGA's) or Application Specific Integrated Circuits (ASICs). Implementation of the hardware so as to perform the functions described herein will be apparent to persons skilled in the relevant art.

In another embodiment, the invention is implemented using a combination of both hardware and software. In addition, the computer system preferably includes a user interface having a display, which can be any device for displaying information in graphical form, a device for inserting characters, such as a keyboard, a device for indicating screen position, such as a cursor, and a device for the identification of the active location such as a mouse.

Although embodiments of the present invention are described in terms of the exemplary computer system described herein, it will be apparent to a person skilled in the relevant art how to implement the invention using other computer systems and/or computer architectures.

As envisioned by the present invention, the computer system possesses or may access a database of sequences, where the database is searchable. As used herein, the term "searchable" means the ability of data or files of the database, such as encoded sequences, to be looked into in an effort to find or discover such data or files. The sequence of the database may include a variety of types of sequence data.

Thus, in one embodiment, the present invention relates to methods of comparing sequential data including providing a target sequence and a query sequence, where each sequence is encoded as a set of at least two n-bit binary strings. Furthermore, each bit of each binary string of a sequence is aligned with the corresponding bit of the other binary string, thereby identifying n groups of aligned bits, where each group of aligned bits defines an identity of a component of a sequence. The methods further include determining, by an ordered comparison of the binary strings of the query sequence with the corresponding binary strings of the sequences of the database, an exact or partial match between the query sequence and the sequence of the database, and generating an indication of a match of the target and query sequences based on the ordered comparison.

FIG. 1 is a flowchart that depicts a process that can be used for encoding and searching sequential data. The process begins with step 1, where a symbol feature map and associated statistics are generated. Next, in step 2, sieves representing each sequence are generated and stored. Next, as indicated by step 3, a probe or query sieve may be used to find a similar sieve or set of similar set of sieves based on the scoring established in Step 1. As indicated by step 4, the sieves identified in step 3 may optionally be ordered, such as for viewing.

A benefit of the present invention is that it makes it possible to use existing bit-vector search strategies and obtain uniquely meaningful results. Using sets of binary strings to represent sequences and then applying an "ordered comparison" of these strings obtain this benefit. As used herein, the term "ordered comparison" refers to a comparison of sequences, where each sequence is represented by a set of binary strings and each binary string of a sequence is compared with a corresponding binary string of the sequence being compared. Further, the comparison of the corresponding strings is ordered such that the comparison of at least one pair of corresponding binary strings is dependent upon the results of a comparison of a different pair of corresponding binary strings in the sets belonging to the compared sequences. For example, an ordered comparison may include first detecting a match between a first binary string of a query sequence and a first binary string of a target sequence, thereby identifying a candidate sequence match, and second, where a match is detected between the corresponding first binary strings of the query and target sequences, the order comparison further includes comparing a second binary string of the query sequence and a second binary string of the target sequence at the same index location. Depending on the match criteria selected, for example, by a user, the comparison of the second corresponding binary string pair is dependent upon the results of the comparison of the first binary string pair. For example, if the match criterion requires an exact match between sequences, then the comparison of the second binary string pair is dependent upon the detecting of an exact match between the first pair of corresponding binary strings. Where the match criterion is a partial match the comparison of the second binary string pair may be limited, for example, to only index positions where the mismatch results in an acceptably high score in accordance with a pre-determined scoring table for mismatches. In this manner, the results of the first comparison step influence the comparison made at the second step.

The resulting matches are novel, useful and flexible because they are based on matching a wide variety of features derived from the original sequences and embodied as bit-vectors. Moreover, the resulting overall methodology is very fast because approximate string matching can now be done on a set of bit-vectors using linear time ($O(n)$) methods.

The term "corresponding binary strings" as used herein, refer to binary strings of sequences being compared that are appropriate for the comparison and maintain the significance of the encoding of the sequences according to the present invention. Such corresponding binary strings will be apparent to one skilled in the art, viewing the current disclosure.

The term "similarly encoded" as used herein, refer to an identical encoding scheme, applied to separate sequences, that is capable of maintaining the significance of the encoding of the sequences, and enable meaningful comparison, according to the methods and systems of the current invention.

Corresponding binary strings, and, therefore, sequences encoded as a set of at least two binary strings, may be compared in a manner consistent with a logical computer operation. A comparison of sequences according to the present invention may identify a variety of matches or a determination of the degree of sequence identity. In one embodiment, a match may include an exact match or identical match, between the query sequence and one of the sequences subject to comparison.

The terms "identical", "percent identity" or "degree of sequence identity" refer to two or more sequences or subsequences that are the same or have a specified percentage of sequence components that are the same, when compared and aligned for maximum correspondence, as measured using a sequence comparison algorithm or methods of the current invention. A match may further include a partial match of sequence components. A partial match is a match in less then the entirety of sequence components being compared. Partial matches are discussed in greater detail below. In another embodiment, a comparison is capable of identifying mismatching sequence components.

The term "sequence", in computer science, refers to a string of symbols. In bioinformatics, "sequence" refers to a string of symbols signifying a biomolecular sequence (e.g. the DNA sequence for a gene, the amino acid sequence for a protein).

The term "biometrics" refers to identifying an individual based on his or her physiological or behavioral characteristics.

The term "feature extraction" refers to the art of extracting specific kinds of information, broadly defined as "features", from various kinds of signals including image data, speech data, keystroke data, sequence data, etc.

"Approximate string matching" refers to a process for comparing two sequences as follows: Given a text sequence T, a probe sequence P and a maximal number of differences permitted, k, approximate string matching finds all the text positions where the probe matches the text up to k differences. The differences can be due to substituting, deleting or inserting a symbol.

The term "sequence alignment" refers to the process of approximate string matching commonly applied to biomolecular sequence data but which may also be used for approximate matching of sequences arising from other applications.

The term "similarity-finding" is a general term for identifying functional, structural or sequential similarities between biomolecular sequences. When applied to sequences, similarity-finding often refers to sequence alignment.

The term "homology" means having common ancestry. Homologous sequences are biomolecular sequences that share common ancestors somewhere deep in the tree of evolution.

The term "sieve" refers to a set of bit-strings derived from a sequence of symbols. Given a sequence of symbols $$S = \{s_1, s_2, \ldots s_m\},$$

we define a sieve to be a set of bit-vectors, $$V = \{v_1, v_2, \ldots, v_n\},$$

where $$v_i = f_i(S)$$

and $f_i$ is a well-defined function mapping each symbol or set of symbols in S to either a 0 or 1 such that if the feature is present or true for the symbol(s) at a given position i in a sequence, then the $i^{th}$ h position in the bit-vector is set to one (1), otherwise it is set to zero (0).

The terms "bit-vector" and "binary string" are generally herein used interchangeably. It will further be understood that a bit-vector may be written as a binary string but that a binary string is not necessarily a vector in any measure space.

The term "match" means to compare—whether two sequences match is determined by how they are compared. Therefore, both the definition of matching and the strength or goodness of a match is tied to the method of comparison. Computationally; matching may be exact or approximate. A match may be based on scientific knowledge of functional similarity. The concept of "good match" and "insufficient match" is determined broadly by criteria including, but not restricted to, user choice, scientific knowledge and search strategy. For instance, a "good match" may be interpreted as an exact match, where every element in one binary string is identical to every element in a second binary string. Alternatively, a good match may mean a sufficiently long partial match, where several consecutive elements of one binary string are identical to several consecutive elements in part of the second binary string. Partial matching may also be referred to as the approximate string matching of bit-vectors. The goodness of such a match may be determined by setting the number of allowed differences or by establishing a scoring system based on the nature of the mismatches. Finally, a match may be determined by scientific or common knowledge—for example, two sequences are already known to represent proteins with the same structure or two sentences are known to say basically the same thing.

The term "scoring" refers to the means by which a match strength or goodness within a given computational strategy is determined. For example, when comparing two strings exactly, scores usually simply count up the number of differences between two strings given a specific alignment. In another example, when comparing strings for approximate matches, scoring may be determined by the state of the automata as the comparison process progresses. Such scoring may simply take the form of a counter that is incremented or decremented as different states are entered or left. In an embodiment of the present invention, scoring has a hierarchical character, where each binary string comparison within a sieve achieves a score and also where the sieve as a whole achieves a score based on the weighted set of its constituent scores.

Criteria for a match may be selected, by a user, for example, prior to the ordered comparison. As used herein, the term "user" includes a person that utilizes a method of the invention or interacts with a computer system of the current invention. A user may select the criteria for a match, for example, by providing instructions to the computer system, such as by providing software or through interaction with the user interface. The results of the comparison may be displayed according to the criteria selected prior to the ordered comparison.

In one embodiment, the sequences of the invention include nucleic acid sequences or nucleotide sequences. Nucleotide sequences of the inventive methods each may be similarly encoded, for example, as a set of two binary strings.

In one embodiment of the invention, nucleotide sequences of the database may each be associated with a particular phenotype or characteristic associated with the expression of a gene.

The terms "nucleic acid sequence", "nucleotide sequence", and "polynucleotide" refer to DNA or RNA. There is no theoretical limitation as to the length of a polynucleotide or nucleic acid sequence and the practical limitations are dependent on the capacity of the specific computer system employed.

The term "expression of a gene" refers to the process wherein a DNA region is transcribed into an RNA which is biologically active including, for example, being either capable of interaction with another nucleic acid or capable of being translated into a polypeptide or protein.

The term "phenotype" or "phenotypic trait" is associated with the phenotypic expression of a nucleic acid of interest and refers to any quantitative or qualitative characteristic or trait, as well as the direct or indirect effect mediated upon the cell, or the organism containing that cell, by the presence of the RNA molecules, peptide or protein, or post-translationally modified peptide or protein.

An example of such a phenotype or characteristic may include, for example, at least one characteristic relating to the capability of an individual to metabolize a drug or compound, or "drug metabolism characteristic". Such a characteristic may relate, for example, to metabolic kinetics of a drug, or pharmacokinetics, such as the clearance rate of a drug from a patient's body or the rate of metabolic conversion. In such an embodiment, the results of a comparison of sequences may include a prediction of at least one drug metabolism characteristic associated with the query sequence. A method may further include selecting a drug therapy based on the results of such a comparison. The term "drug therapy" may refer, for example, to both the selection of a particular drug and to the dosage amount of the drug.

The term "Coding sequence" refers to a nucleotide sequence that codes for a specific amino acid sequence.

The term "Promoter" refers to a nucleotide sequence capable of controlling the expression of a coding sequence.

The term "amplified" refers to the construction of multiple copies of a nucleic acid sequence or multiple copies complementary to the nucleic acid sequence using at least one of the nucleic acid sequences as a template. Amplification systems include the polymerase chain reaction (PCR) system, ligase chain reaction (LCR) system, nucleic acid sequence based amplification (NASBA, Cangene, Mississauga, Ontario), Q-Beta Replicase systems, transcription-based amplification system (TAS), and strand displacement amplification (SDA). See, e.g., Diagnostic Molecular Microbiology: Principles and Applications, D. H. Persing et al., Ed., American Society for Microbiology, Washington, D.C. (1993).

The term "Polymerase chain reaction" ("PCR") refers to a method for increasing the concentration of a segment in a target sequence (U.S. Pat. Nos. 4,683,195; 4,683,202; and 4,965,188, hereby incorporated by reference).

The term "Pharmacogenomics" refers to the study of the inherited basis of differences in response to drugs.

The present invention further includes methods of identifying matching nucleotide sequence data. Such methods include providing a searchable database of nucleotide sequences encoded as a set of two binary strings, and providing a query nucleotide sequence similarly encoded as a set of two binary strings. The methods further include detecting a match between a first binary string of the query nucleotide sequence and a first binary string of a nucleotide sequence of the database, thereby identifying a candidate nucleotide sequence match, and detecting a match between a second binary string of the query nucleotide sequence and a second binary string of the candidate nucleotide sequence match, thereby identifying a sequence match between the query nucleotide sequence and the nucleotide sequence of the database.

In another embodiment, the sequences of the invention may include amino acid sequences. In such an embodiment, each sequence may be encoded as a set of at least five binary strings. The method may further include scoring mismatching amino acids of the compared sequences based on the identities of the amino acids aligned in the comparison. Scoring mismatching amino acids may include, for example, using a scoring matrix such as PAM or BLOSUM. Amino acids sequences of the comparison may be of a variety of lengths. The method provides flexibility to use alternate scoring methods based on the partial matches of subsets of the complete set of binary strings.

In one embodiment, sequences of the invention may comprise lexicographic sequences. See, for example, Example 4 provided below.

Sequences of the present invention may also include sequences derived from biometric data. Biometric data includes data having information about certain unique body characteristics including, for example, fingerprints, retinal scans, facial recognition and voice pattern authentication. Biometric data may be encoded according to the present invention and encoded sequences may be associated with a characteristic or identity of a subject. Voice verification, which is also known as voice authentication, voice pattern authentication, speaker identity verification and voice print, may be used to provide the speaker identification. The terms voice verification and voice authentication are interchangeably used herein. Techniques of voice verification have been extensively described in U.S. Pat. Nos. 5,502,759; 5,499,288; 5,414,755; 5,365,574; 5,297,194; 5,216,720; 5,142,565; 5,127,043; 5,054,083; 5,023,901; 4,468,204 and 4,100,370, all of which are incorporated by reference as if fully set forth herein. These patents describe numerous methods for voice verification.

Voice authentication seeks to identify the speaker based on a spoken utterance. For example, a speaker's presumed identity may be verified using feature extraction and pattern matching algorithms, wherein pattern matching is performed between features of a digitized incoming voice print and those of previously stored reference samples. Features used for speech processing involve, for example, pitch frequency, power spectrum values, spectrum coefficients and linear predictive coding (see, for example, B. S. Atal (1976) Automatic recognition of speakers from their voice. Proc. IEEE, Vol. 64, pp. 460-475, which is incorporated by reference as if fully set forth herein).

Alternative techniques for voice identification include, but are not limited to, neural network processing, comparison of a voice pattern with a reference set, verification using selectively adjustable signal thresholds, and simultaneous voice recognition and verification.

Feature classification techniques are described in S. Furui (1991) Speaker dependent—feature extraction, recognition and processing techniques. Speech communications, Vol. 10, pp. 505-520, which is incorporated by reference as if fully set forth herein.

In yet another embodiment, sequences of the invention may comprise phonetic sequences. In such an instance, each sequence component includes a phoneme. In another embodiment, the sequences comprise speech pattern sequences. Such speech pattern sequences may include duration, frequency or intonation speech data. A speech pattern sequence also may include formant pattern data. Speech pattern sequences, such as those sequences in a database, may each be associated with a particular speaker. In such an instance, a comparison of sequences may allow for the identification of a speaker. See, for example, Examples 5 and 6 provided below.

In another embodiment, sequences may represent characteristic patterns related to fingerprints. In one implementation, the sequence components may correspond to recognizable features of the ridges such as bifurcations or terminations which are termed minutia. These may be arranged into an ordered sequence based on their location on the scanned image and used to compare the pattern of a subject with sequences in a stored data base. Additional details are provided in Example 7 below.

In another embodiment, sequences of the invention may include signal analysis sequences. Signal analysis sequences may include electromagnetic data, optical data, acoustic data, or seismic data sequences. Where signal analysis sequences include seismic data sequences, certain seismic data sequences, such as those in a database, may be associated with an earthquake activity profile or the presence of an oil-bearing subsurface dome structure. As such, the results of a comparison of such sequences may include a prediction of earthquake activity or the location of promising oil deposits. Additionally, seismic data sequences, such as those in a database, may each be associated with a particular volcanic activity profile, and the results of a comparison of such sequences may include a prediction of volcanic activity. In another instance, signal analysis sequences may be radar data sequences. In yet another instance, signal analysis sequences may include sonar data sequences. In an instance where signal analysis sequences include continuous sequence data, the continuous sequence data may be divided into discrete subsets prior to encoding the signal analysis sequences each as a set of multiple binary strings. See, for example, Example 8 provided below.

In yet another embodiment of the invention, sequences may include data derived from a graphic image. A graphic image may include an x-ray image, CAT scan image, or a Magnetic Resonance Image (MRI image). Such graphic images may be converted to sequential data by scanning and compared with sequences known to correspond to a particular medical condition or medical diagnosis. In such an instance, a comparison of sequences may produce a prediction of a medical condition or diagnosis. In another example, a graphic image may include a television image. In such a case, the data of a graphic image may include pixel location data. In another example, a graphic image may include a fingerprint image. In yet anther example, a graphic image may include a photographic image. See, for example, Examples 9 and 12, provided below.

In another embodiment, sequences of the invention may include sequential data derived from an interactive game. Data derived from an interactive game may include, for example, a series of executable moves or steps, or a state of at least one executable element. In such an embodiment the results of a comparison of sequences may include a prediction of a game outcome. A variety of interactive games are herein envisioned. One such interactive game includes chess. See, for example, Example 10, provided below.

In yet another embodiment, sequences of the invention may include law enforcement related sequence data useful in solving a crime or in identifying an individual. Law enforcement related sequence data may include, for example, fingerprint data, voiceprint data, modus operandi or genetic profile data. Accordingly, a sequence, such as a sequence in a database, may be associated with the identity of a subject or individual, and the results of a comparison of sequences may include a prediction of a subject's identity. See, for example, Example 11, provided below.

In another embodiment, sequences of the invention may include temporal sequence data related to the status of mechanical equipment. Status may include, for example, timed readings of temperature, pressure, strains, or other gauges. Such sequence data may include a series of measurements recorded at regular time intervals and compared with sequences known to predict mechanical failure. See, for example, Example 13, provided below.

The present invention further includes methods of comparing at least two gene expression profiles. The methods include providing a subject expression profile of a sample from subject, where the subject expression profile is encoded as a set of at least two binary strings, and providing a plurality of reference profiles, each reference profile similarly encoded as a set of at least two binary strings, where the subject expression profile and each reference profile has a plurality of values, each value representing the expression level of a gene. The method further includes comparing, by an ordered comparison of the binary strings of the subject expression profile sequence with the corresponding binary strings of at least one reference profile sequence, the reference profile and the subject expression profile.

The term "gene expression profile" as used herein, refers to data reflecting levels of expression of a plurality of genes in a sample. The sample may be obtained from a subject and analyzed for gene expression. Gene expression data may be derived, for example, from a micro-array analysis. Gene expression data may, for example, be expressed as a ratio of fluorescence. In one embodiment, a gene expression profile may be a whole-genome analysis.

In one embodiment, a gene expression profile, such as a reference profile, may be associated with a particular condition. For example, a condition may be either the presence or absence of a particular disease.

The following examples are intended to illustrate but not limit the invention.

EXAMPLE 1

Genomics

This example illustrates that the current system and methods may be successfully utilized in the field of bioinformatics, for the collection, classification, storage, and analysis of biochemical and biological information using computers, particularly as applied in molecular genetics and genomics.

Nucleotide sequences are typically stored as sequences, often of great length, consisting of the 4 bases A (Adenine), G(Guanine), T(Thymine), and C(Cytosine). For example, a sequence might be:

(SEQ ID NO: 1)
GATACCTTAGGAACTGAAAAAGGATTCAGGACTG...

Each of the 4 bases is represented by an alphabetic symbol and such symbols in a computer have typically been stored in previous systems as a byte or block of 8 bit locations, so that a sequence of length N would require 8×N bits of storage space. Searches for alignment are perhaps the most common of all nucleotide sequence analyses and typically consist, for simple local alignments, of trying to match a shorter query (for example, a test, probe, sample, or pattern) sequence with one or many much longer target or reference sequences in order to find all positions, i.e., target sequence index locations, where the query sequence aligns with the target sequence. For example, using the above sequence as a target and the simple query sequence ACTG, the following exact alignments (identified below in bolded text) would be found:

(SEQ ID NO: 1)
GATACCTTAGGAACTGAAAAAGGATTCAGGACTG...

In some applications, the query sequences are comparatively short (for example, 2-20 bases in length) but there may be a very large number of target sequences each of which might be hundreds, thousands or tens of thousands of bases in length. The process requires a matching of the letters of the query sequence with those of the target sequence(s) as the query sequence is indexed along the length.

The current invention includes representing a sequence component, regardless of the length of the sequence, as a set of at least two binary strings equal in length to the sequence represented. Where the sequence is a nucleotide sequence, the sequence may be encoded, for example, as a set of exactly two binary strings. Thus the example sequence could be represented as the following pair of binary strings:
10001100011001010000011000110101...
10100011011000110000011011001110011...

In forming these two separate strings the following exemplary representation have been assigned:

$$\begin{array}{cccc} 0 & 1 & 0 & 1 \\ A=0, & G=1, & T=1, \text{ and } & C=0 \end{array}$$

Thus, the query sequence ACTG would be represented as the following pair of binary strings:
0101
0011
and the resulting parallel alignment of the binary strings of the target sequence would be as follows:
10001100011001010000011000110101...
10100011011000110000011011001110011...

It is important to distinguish between encoding a sequence into a set of parallel binary strings, as utilized in the current invention, and simply replacing the sequence components, including the letters A,G,T,C, in the original sequence by the pairs {00}, {11}, {01}, {10} to convert the original sequence into a single linear binary sequence of double the length of the original. The latter encoding is illustrated below (spaces have been introduced to illustrate the correspondence and would not appear in the final form of the converted binary string):

```
                                                (SEQ ID NO: 1)
G A T A C C T TAGGAACTGAAAAAGGATTCAGGACTG...
11 00 01 00 10 10 01 01....etc.
```

This form of encoding may be referred to as the 'in-line' substitution to distinguish it from the parallel encoding. The in-line encoding is only a minor modification of substituting the ASCI-8-bite codes for the letters AGTC and would require matching 2-bit strings of a query against 2-bit strings of the target. This involves more computation at each index position than simply matching of single-bit binary strings. It may be noted, however, that the simple binary string encoding of the preferred parallel alignment method can be implemented by selecting for the first binary string the odd numbered elements of the in-line encoding and for the second binary string, the even-numbered elements of the in-line representation. Such selection might be conveniently achieved by means of a mask. The end result is entirely equivalent to the proposed creation of a set of two parallel binary strings in separate registers. There may be many methods for decomposing the information content of the sequences into sets of two or more simpler sequences. The present invention is intended to encompass whatever means is used to generate or store the sets of simpler partial test sequences. The power of the novel decomposition derives from the fact that each of the two simple binary strings represents a necessary condition for a match and consequently each one alone identifies the only candidate positions that need to be verified by checking the companion binary strings. Hence it acts as a sieve or filter to reduce the space to be searched. In the present example, if the first binary string of the query 0101 is tested against the first binary string of the target sequence 10001100011001010000011000101101010, this test alone narrows the search to only the three candidate index positions shown in bold: 10001100011001010000011000101101010.

The second binary string of the query sequence need only be checked at these index locations against the second binary string of the target sequence to determine which of these candidate matches are true identities.

Short query sequences (such as AGTC) do not fully reveal the power of the current invention since at any index position, the probability of exactly matching a pattern of four ones and zeros would be (½) to the 4th power or ¹⁄₁₆ for a completely random string of four binary bits. However, if the query sequence is of length M, the probability of an exact random match at any given index position becomes (½) to the Mth power. For typical DNA query sequences of length 10 or 20, the probability of a random match at any index position would be ½ to the 10th power or ½ to the 20th power respectively. Consequently, each of the independent binary strings of the parallel decomposition serves to identify relatively few candidate matches and hence narrows dramatically the index positions where the companion binary strings need to be checked to verify that a true match has been located.

As an example, one may consider a query sequence of 10 nucleotides searching a library containing 50,000 reference sequences each of which is 1000 nucleotides in length.

For a query sequence of length 10, the probability of a match with a random binary sequence is approximately ¹⁄₁₀₀₀ at each index position so that the expected number of 'hits' when tested against each reference sequence in the library is only one false 'hit' (on the average) for each sequence in the library. The remaining hits represent true matches and the number of such hits depends on how frequently the true pattern is found in the sequences of the library. Only the specific locations where a (true or random) hit is found by the first binary string need to be tested against the second binary string to confirm a true identity match. If the query sequence was 20 nucleotides in length, the probability of matching a random sequence is approximately 1 in one million so that only 50 random or false matches would be expected in the entire reference database of 50,000 target sequences each such sequence being 1000 nucleotides in length.

As a realistic illustration, the following sequence (SEQ ID NO:2) taken from HIV2BEN [GI:1332355] of the National Institute of Health database is shown both in the usual format and in the parallel decomposed form. The query sub-sequence ctatgtccat is shown in bold starting at index 1531. The method would represent the query sequence as the two parallel strings 1000101100 and 0101110001. The 'hits' resulting from each of these strings are shown in bold. In addition to the true match starting at index 1531 there was only one false 'hit' using the first string (at index 1433) and no false 'hits' from the second string.

```
1021 gtgaaggtaa gtacctacac caaaaactgt agccagaaaa ggcttgttat cctaccttta
     1010011000 1001100101 1000001010 0111010000 1110010000 1100110000
     1110011100 1100010000 0000000111 0100010000 1101111101 0010001110

1081 gacaggtaga agattgtggg agatgggcgc gagaaactcc gtcttgagag ggaaaaaagc
     1010110010 0100010111 0100111111 1010001011 1010010101 1100000011
     1000111010 0101111111 0101111010 1010000100 1101110101 1100000010

1141 agacgaatta gaaaaagtta ggttacggcc cggcggaaag aaaaagtaca ggttaaaaca
     0101100000 1000001000 1100011111 1111110001 0000010010 1100000010
     0100100110 1000001110 1111001100 0110110001 0000011000 1111000000

1201 tattgtgtgg gcagcgaatg aattggataa attcggattg gcagagagcc tgttggagtc
     0000101011 1101110001 0000110000 0001110001 1101010111 0100110101
     1011111111 1001010011 0011110100 0110110111 1001010100 1111110110

1261 aaaagaaggt tgccaaaaga ttctcagagt tttagatcca ttagtaccaa cagggtcaga
     0000100110 0111000010 0010101010 0000100110 0001001100 1011101010
     0000100111 1100000010 1101001011 1110101000 1101100000 0011110010

1321 aaatttaaaa agccttttta ataccgtctg cgtcatttgg tgcttgcacg cagaagagaa
     0000000000 0111000000 0001110101 1101000011 0110011011 1010010100
     0001110000 0100111110 0100011011 0110011111 1101110001 0010010100
```

```
1381 agtgaaagat actgaggaag caaagaaact agcacagaga catctagtgg cagaaactgg
     0101000100 0101011001 1000100010 0110101010 1001001011 1010001011
     0111000101 0011011001 0000100001 0100001010 0010101111 0010000100

1441 aactgcagag aaaatgccaa atacaagtag accaacagca ccacctagtg ggaaaagagg
     0010110101 0000011100 0001001001 0110010110 1101100101 1100001011
     0001100101 0000110000 0100001101 0001100100 0000010111 1100001011

1501 aaactacccc gtgcaacaag cgggtggcaa ctatgtccat gtgccactga gcccccgaac
     0001001111 1011001001 1111011100 1000101100 1011101010 1111111001
     0000100000 1110000001 0111111000 0101110001 1110000110 1000001000

1561 tctaaatgca tgggtaaaat tagtggagga aaagaagttc ggggcagaag tagtgccagg
     0100000110 0111000000 0010110110 0001001001 1111101001 0010111011
     1010001100 1111100001 1011110110 0001001110 1111001001 1011100011

1621 atttcaggca ctctcagaag gctgcacgcc ctatgatatt aatcaaatgc ttaattgtgt
     0000101110 1010101001 1101101111 1000100000 0001000011 0000001010
     0111001100 0101001001 1011000100 0101101011 0010000110 1100111111

1681 gggcgatcac caagcagcta tgcaaataat cagagagatt attaatgaag aagcagcaga
     1111100101 1001101100 0110000000 1010101000 0000001001 0011011010
     1110101000 0001001010 1100001001 0010101011 0110011001 0010010010

1741 ctgggattcg cagcacccaa taccaggccc cttaccagca ggacagctca gagacccaag
     1011100011 1011011100 0011011111 1000110110 1101011010 1010111001
     0111101101 0010000000 1000011000 0110000100 1100010100 1010000001

1801 agggtctgac atagcaggaa caacaagcac agtagatgaa cagatccagt ggatgtatag
     0111010101 0001101100 1001001101 0100100100 1010011010 1100100001
     0111101100 0101001100 0000001000 0110101100 0010100011 1101110101
```

If parallel computers are employed, the second binary string of the query decomposition can be compared to the second binary string of the target sequence at the same time that the first binary strings are being compared without additional time required. There are additional advantages in simplicity and speed that follow from the parallel decomposition compared to the in-line representation that are further addressed below.

The specific representation chosen for the letters A,G,T,C, is not, in itself, unique since there are four choices for A, then 3 choices for C, and then 2 choices for T or 24 possible ways to this encoding. The particular one chosen for illustration has some special useful characteristics that will be described below. An alternate assignment that would capture certain biochemical properties in addition to expediting the pattern search would be to assign to the purines A and G the following respective representations:

1     1

0 and 1

The pyrimidines C and T may be assigned the following respective representations:

0     0

0 and 1

With these representations, the bit appearing in the first binary string identifies the nucleotide as a purine or a pyrimidine and the bit appearing in the second binary string identifies the functional group as the keto or the amino group respectively. As such, a combination of less then the entirety of binary string components at an index location defines an aspect of a sequence component. In the present example, the aspect is identity as either a purine or pyrimidine. Such assignments may be selected by the user for the particular search application being considered. It should be recognized that any of the 24 possible assignments will result in shortening the search time to find a matching pattern.

For any representation assignment, the storage is also reduced from 8×N bits to 2×N bits for a sequence of length N. This latter observation is true of the 'in-line' representation as well as for the parallel decomposition.

All variations of specific assignment of a particular binary code to each element (member) of the original sequence in this as well as all other application areas (where more than two binary strings may required) are intended to be included in the patent.

Complementary Strand

When the sequence of nucleotides represents one strand of the DNA double helix, the second or complementary strand is related to the given 'sensing' strand and includes the same 4 bases. These are connected to the sensing strand by the bonding of A-T and G-C. The following strand is presented by way of example: for the strand (SEQ ID NO: 1)
GATACCTTAGGAACTGAAAAAGGATTCAGGACTG...............
.....the related strand (SEQ ID NO: 3)
CTATGGAATCCTTGACTTTTTCCTAAGTCCTGAC.......
...would be the complement With the particular exemplified binary assignment to the letters A, G, T, and C, the encoding of the complementary strand can be obtained from the encoding of the sensing strand immediately since the first binary string is exactly the same and the second binary string of the complementary strand is simply the 2's complement of the second string of the sense strand, as illustrated by the following representation:
    10001100011001010000011000010110101 ...
    0101110010011100111110010011001100       . . .

This simplicity in determining the complementary strand is not present in the in-line representation but follows immediately from the parallel decomposition.

Exact Alignment Searches

For an exact search of a DNA sequence, an alignment requires that the first binary string of the decomposed query sequence align with the first binary string of the target sequence and the second string of the query align with the second string of the target at the same index positions. Each of the matches is a necessary condition for an alignment and both are required for a sufficient condition. Thus if the check of the first binary string finds no exact alignments it is not necessary to check the second binary strings. Also, if there are alignments found that match the first query string against the first target string, only those particular index positions need to be checked for agreement of the second query string against the second target string. Note that the tests of the first and second strings are independent and hence are easily adapted to parallel processing methods.

The nature of the ordered comparison matching process itself also affords a very substantial saving in processing time. Instead of checking agreement of the alphabetic letters, it is only necessary to perform the bit-logical summation (essentially the Boolean 'exclusive or' operation; A or B but not both). This is an inherent operation intrinsic to digital computers and consists of adding bits without carryover. Thus 0+0=0, 1+0=1, 0+1=1, and 1+1=0. It is this last case which invokes the non-carryover property. With this form of addition, the test for a match is simply that the sum is zero at each of the bit locations being tested. A non-zero confirms a mismatch but a zero result only identifies a candidate match that needs to be confirmed by the second or additional subsequent corresponding pair.

A further efficient property of digital computers that this form of representation now permits is to use a shift register to perform the indexing operation. Again an operation which is at the inherent level of digital processors. If the target sequence is of length N (for example, a large sequence) and the query sequence is of length M (for example, a sequence shorter then the target sequence), the number of index positions that would seem necessary to be checked would be (N-M) to try all the positions of the query against the target. However, it is possible to replicate the short query sequence by adding tandem copies of itself until it is at least of equal length to the target sequence. For the short query ACTG which, in the parallel binary form is
0101
0011, the extended form of ACTG would now become
0101010101010101010101010101010101010101 . . .
0011001100110011001100110011001100110011 . . .

Then the two long sequences of the extended first query string against the first target string are subjected to a 'no-carry' bit summation and only those blocks that show M consecutive zeros need to be checked by the second query string (extended) against the second target string. The advantage of the tandem extension is that now only M index (or shift) operations are needed to test all possible alignments for exact matches instead of (N-M) shifts, thereby increasing search or comparison efficiency.

The simplicity and computational efficiency of the parallel decomposition relative to the in-line representation is illustrated by both of the properties described above; namely that the comparison is a bit-bit logical operation and that checking the various index positions involves a sequence of one bit shifts or single bit shifts.

Mutations

One of the frequent purposes of searches of nucleotide sequences is the attempt to locate mutations. Although there may be more than one base change in a particular coding sequence, the search may be for a Single Nucleotide Polymorphism (SNP), for example, in which a single base in a region of interest (for example, an exon region) has been changed. This may result in an altered or defective protein depending on the specific region and the particular change. To illustrate how the current invention and methods simplify such searches, the following exemplary sequence is provided (taken from a small part of a yeast gene): GCAGCGCACGA-CAGCTGTGCTATCCCGGCGAGCCCG . . . (SEQ ID NO:4).

When converted to a pair of binary strings by the method previously described, this sequence is represented as follows:
1101111011001101011000111111101111 . . .
1001010001000101111010100011010100001 . . .

If the original sequence has a mutation in the position shown below in bold and underlined: GCAGCGCACGA-CAGCTGTGCTATCCCGGCGACCCCG . . . (SEQ ID NO:5).

The changes to the pair of binary strings to correspond to the indicated change from a G to a C would result as the following set of binary strings:
1101111011010110101100011111101111 . . .
1001010001001011110101000110100001 . . .

If the original binary strings and the binary strings for the mutant form are subtracted, everything will be zero except in the 30th index position so that the location and type of mutation become immediately evident. This works equally well for multiple mutations as for Single Nucleotide Polymorphisms.

Accordingly, in locating a mutation in a large sequence, the novel method is simply to subtract two binary strings, one representing the 'standard' form of the sequence and the other representing the mutated form. If there is no mutation, the result is all zeros. If there is a mutation (or several) these will appear as non-zeros. This is faster and easier than any previously existing method since it is simply a numerical subtraction of two binary strings (for each member of the set of parallel binary strings with its corresponding opposite number.) Since these are already in binary form, the operation is extremely fast compared with any other method of doing this. There is no limitation on the length of the sequence even if the computer being used has string lengths limited to 32, 64 or 128 bits since it is not difficult to invoke double precision, triple precision, etc. as necessary or to partition the sequence(s) into several parts to accommodate whatever maximum string length may exist. There are freely available methods for the efficient handling of extremely long binary strings (for example, on the world wide web "www" at the url "nersc.gov/~dhbailey/").

Common Regions of Identity

The method of the invention is also useful where it is desirable to locate those regions where two (possibly long) sequences share identical sub-sequences in common. Such searches consider all possible shifts of one sequence relative to the other and attempt to locate all common regions of identical sub-sequences. One of the earliest (but still used) techniques for finding such regions is the DOTLET method. This is illustrated below for the following two sequences:

AGGTACTCGACT. . . . .    (SEQ ID NO: 6)

GCCTATGACTCGA. . . .    (SEQ ID NO: 7)

A matrix is created with one of the sequences along the horizontal axis and one along the vertical axis and a mark or "dot" (in the present example the symbol "+" is used for the dot) is then placed in each position of each row where there is a match as shown below:

```
                                    (SEQ ID NO: 6)
     A G G T A C T C G A C T...
   G + +         +
   C         +   +     +
   C         +   +     +
   T     +       +        +
   A +       +       +
   T         +   +        +
   G + +             +
   A +       +       +
   C         +   +     +
   T     +       +        +
   C         +   +     +
   G + +             +
   A +       +       +
```

Regions of alignment are indicated by consecutive entries on a diagonal. In this case, the two sub-sequences ACTCGA and also GACT are evident. This classical method requires comparisons of each letter of the column against every letter of the top row. Each such comparison is a byte-matching operation. For sequences of lengths M and N, the total number of such byte-matching operations is M×N. However, if the comparison is made using the present invention, the sequences are each represented by two binary strings, and the process becomes computationally much simpler. The two sequences used in the example above are now described by the following pairs:

011001011010
011100101001, and
1110001010110
1001011001010

There are now two 'Dotlet' matrices to consider; one formed using the first binary string of the first sequence on the horizontal paired with the first binary string of the second sequence on the vertical. A similar matrix is formed using the second binary strings of each sequence as follows:

```
    011001011010     0111001010 01

1  011001011010  1  011100101001
  1  011001011010  0  100011010110
  1  011001011010  0  100011010110
  0  100110100101  1  011100101001
  0  100110100101  0  100011010110
  0  100110100101  1  011100101001
  1  011001011010  1  011100101001
  0  100110100101  0  100011010110
  1  011001011010  0  100011010110
  0  100110100101  1  011100101001
  1  011001011010  0  100011010110
  1  011001011010  1  011100101001
  0  100110100101  0  100011010110
```

The entries of each of these matrices have been filled by extremely efficient operations. If there is a "1" in the left column, then the entire binary string along the top is simply copied into that entire row, if there is a "0" then the binary complement is entered into the row. In effect, the binary string at the top flows down thru the array and is either entered intact or as the bit complement in each row regardless of the length of that row. The final step is to combine the two matrices with the logical 'and' operation so that only those locations where both arrays have a "1" will be chosen. The result, of course, is the same as in the classical approach.

CpG Islands: In vertebrate DNA sequences, the di-nucleotide sequence "CG" is quite rare since methylation forces the CG to become CT. However, in the very important promoter regions which signal the approach of a coding region and in the coding region of the DNA itself, the methylation process is suppressed and the presence of CG sequences increases dramatically. This can be used as a means to locate the portions of the DNA sequence that may contain the exons that code for proteins.

The overall content of a G or a C in the total DNA sequence is about 40%, but in the CpG island regions this increases to 60-70%. Furthermore, the occurrence of adjacent CG di-nucleotide pairs is only about 1% outside of the CpG islands but rises to approximately 10% in CpG islands, a 10-fold increase.

With the present method of encoding DNA sequences, the location of CpG islands is very greatly facilitated since the representations of G and or C are:

$$G = \begin{matrix} 1 \\ 1 \end{matrix} \text{ and } C = \begin{matrix} 1 \\ 0 \end{matrix}$$

Consequently, locating regions that are rich in G's or C's is simply a matter of searching the first string of the two binary strings, for regions rich in "(1's)". The second string is not needed at all if the object of the search is to locate regions that are abnormally rich in (G or C) content.

Furthermore, the search for the very important CG di-nucleotides is also facilitated by this method. The first string of the representation of the DNA sequence of interest is searched by the short pair, "11". If there is a hit, then this is a di-nucleotide that involves only G's and C's. To determine whether it is indeed a CG di-nucleotide (instead of CC or GG or GC), it is only necessary to examine the second string at these positions to find the pair "01" that would confirm that a CG di-nucleotide had been located since an upper string of 11 and a lower string of 01 uniquely defines a CG pair.

Similarly, regions that are rich in A's and T's are of special significance in molecular biology and these can be very easily located since both A and T are represented by a zero in the first binary string. Hence, locating those regions where the first binary string is rich in "0's" is sufficient to locate regions rich in A's and T's. It is also often desirable to locate the so-called 'poly-A' regions which are used as an anchor by the mRNA. In this form of encoding, a string of A's is represented by a long block of zeros in both of the representative binary strings. Those skilled in the art would appreciate that our novel method has additional advantages in that, by the way of example, it may be used to identify promoters, cis-regulatory sequences, identification of shared promoter modules and the identification of the partners in transcriptional co-regulation.

Gene Finding

One of the important steps used to help locate genes in a DNA sequence is to try to identify protein coding regions by characteristic patterns surrounding those regions. There are three broad categories of such patterns.

(1) An initial exon region is typically bounded by a start codon ATG at the beginning of the region and by a splice donor junction GT at the end of the region.

(2) Internal exon regions that are spliced to form the expressed protein are preceded by the pattern of an acceptor junction, {C or T}AG, and terminate with a splice donor junction GT.

(3) Terminal codons are bounded by an acceptor junction, {C or T}AG, and end with a stop codon TAA.

Searches for such patterns are one of the steps currently employed by gene finding systems such as: GeneMark, Genie, GenScan, Glimmer, GRAIL, and Procrustes.

The novel method of representation establishes a correspondence to the short binary sequence pairs for the patterns ATG, GT, {C or T} AG, and TAA respectively.

```
001   10   {any}01   000

011   11   {any}01   100
```

These short arrays of dimension 2×3 or 2×2 can be indexed along the length of the DNA sequence being studied and subtracted (as arrays) from the two binary strings representing that sequence. A hit would then be identified by a 2×3 or 2×2 array of all zeros. This efficient process can be further expedited by incorporating a special purpose module (e.g., a computer chip) that is designed specifically to perform such array operations where the array elements are constrained to be zeros or ones. The technology exists to create such special chips from Field Programmable Gate Arrays.

Partial Matches

It is rare to find very long sequences of nucleic acides (or amino acids) that are in exact agreement, although shorter sequences (for example, 11-25 for nucleic acids or 2-5 for amino acids) are of common use in finding starting locations for powerful alignment programs such as BLAST or FASTA that subsequently extend these exact alignments using dynamic programming algorithms. For partial matches, there is generally a scoring plan established to accept up to a certain number of mismatches of the query against the target. If only a simple count is needed, then the number of "1's" that appear in the index region being tested is one measure of the degree of mismatch. This may be combined using normal addition with the number of "1's" that appear in the same index position when testing the second query string against the second target string. The sum of the scores is then compared to some measure of mismatch acceptance.

Another scoring method (for nucleotides) is to assign a heavier weight (for example, double or triple to a transversion; a mismatch between a purine (Adenine (A), Guanine (G)) and a pyrimidine (Thymine (T), Cytosine (C)). Not all alignment algorithms use a simple scoring of matches and mismatches (or multiples for transversions). There are also various scoring schemes (such as PAM or BLOSUM) employed to assign specific values to particular mismatches. Furthermore, there are often gaps introduced in the query sequence and/or the target sequence in an attempt to find a better overall score for the alignment. This is particularly true for the case of amino acid sequences as further discussed below, but is also common practice for sequences of nucleotides. Among the approaches, algorithms and specific computer codes used for such searches are dynamic programming methods (for example, Smith-Waterman, Needleman-Wunsch, SSEARCH), heuristic methods (for example, FASTA, BLAST), multiple sequence alignment methods (for example, CLUSTALW), methods based on hidden Markov models (for example, hmmbuild, hmmsearch, SAM), clustering methods (for example, hierarchical, k-means, EM-algorithm, Treeview), neural network methods and many others. Specific algorithms and associated computer codes have been developed to implement these approaches. These methods and scoring schemes can be adapted to function using the proposed decomposition of the information content of the sequences into parallel sets of binary strings.

Micro-Array Data Analysis

One common implementation of a micro-array chip in current practice consists of a small glass (or plastic) plate with a very large number (e.g., 10's or 100's or thousands) of specific locations, i.e., "spots". Typically, at each spot there are multiple, identical copies of a probe consisting of an oligonucleotide that represents a single-stranded complementary fragment of a DNA sequence that is known to have been expressed. (The oligonucleotide may be artificially constructed or may be a cDNA fragment obtained by reverse transcriptase.)

One typical experiment is to compare by differential analysis a healthy and a diseased sample. In such an experiment, both the diseased and the healthy sample are amplified by Polymerase Chain Reactions and each is labeled with a different fluorescent marker, e.g. red for the healthy sample and green for the diseased sample. A mixture containing equal portions of the healthy and diseased samples is spread over the surface of the micro-array chip and allowed to hybridize with the complementary single-stranded probes. After removing any excess mixture, each spot of the chip is examined by both a red-sensitive laser and a green-sensitive laser and the ratio (actually the logarithm of the ratio) of red to green at each spot location is determined. The results are grouped into a few finite categories for each spot location such as, for example, strongly red, more red than green, equal, more green than red, strongly green. These would indicate, at each spot location, whether the diseased sample was under-expressed, over-expressed or equivalent to the normal sample. Since the probes corresponded to expressed portions of a DNA sequence (e.g., fragments of genes, for example), these results can be used to determine how the diseased sample proteins may differ from the healthy sample.

With the novel method proposed, the scanning by the lasers produces a sequence. At each index location of the sequence there are a finite number of measures of the relative abundance of red and green markers. Consequently, this sequence can be decomposed into a set of binary strings where the number of binary strings is sufficient to represent the categories used to measure the relative abundance. (For the five categories of ratio of red/green described above, at least three parallel binary strings would be required.) The resulting sequence can then be used as a query against a database of similar sequences for which the nature of the disease is known. A match (or close match) would provide an indication of the nature of the unknown disease being tested. Both the observed sequence from the experiment and the sequences in the database(s) would be represented in the form of parallel binary strings.

Another application of micro-arrays is to study biological processes within cells. This is often referred to as whole-genome analysis. The chip is prepared with fragments of single-stranded oligonucleotides that serve as probes representing all the genes of an organism. A sample under benign conditions is taken as a reference standard. Then the tissue (or other source of the sample) is subjected to some form of environmental stress and samples are taken at selected time intervals. The standard sample and the stressed samples taken at time intervals are amplified and labeled by PCR as above (e.g. red for the unstressed standard sample green for each of the stressed samples). Then, for each time interval, the relative abundance of red and green hybridization can be determined and encoded as prescribed by our novel method. For each time sample, the sequence represents which genes are over-expressed and which are under-expressed. By correlating the sequences at the various time samples, it is possible to infer which genes are co-expressed and hence are involved in the same biological pathways in response to the stressed conditions. The novel encoding simplifies the correlation calculations since these are often in the form of an inner product, which becomes computationally very simple if the elements are all 1's and zero's. The results permit a clustering of the genes in a manner that provides insight into the biological interactions.

EXAMPLE 2

Proteomics

This example illustrates that the current system and methods may be successfully utilized in the field of bioinformatics, for the collection, classification, storage, and analysis of biochemical and biological information using computers, particularly as applied in protein analysis and proteomics.

The primary structure of proteins is represented by a sequence of 20 alphabetic letters corresponding to 20 specific amino acids. An encoding method similar to that used for nucleotides above would require a minimum of 5 digital strings since two to the 5th power is 32 and that is the least power of 2 greater than 20. The specific selection of the encoding may be a assigned by the user and depends upon the intended application. There are more than 24 million distinct ways mathematically to assign a 5-bit code to the 20 amino acids and although only two of these methods are described below as examples, all variations are intended to be covered by this patent.

One way to assign the encoding is to consider the biochemical properties of the amino acids. The amino acids can be chemically grouped into six sets according to their molecular side chains: sulfhydryl, small hydrophilic, acidic (including acid amide and hydrophilic), basic, small hydrophobic, and aromatic. Within each group, the 5-bit encoding would be the same for the first three bits and only differ in the final two bits thus permitting a rapid search where a variation at a given index position that is in the same group is an accepted substitution and would represent a close match to the desired pattern and result in a high score for approximate searches.

Another way to assign the encoding is to consider how the various amino acids in the sequence may influence the resulting structure of the protein. Thus, the assignment may use the initial bits to characterize properties such as strong predictors of alpha-helix structures, beta strands, turns, etc. The remaining bits distinguish the individual amino acids that share these structure-predicting properties.

Another approach is to use 6 binary strings for the encoding of protein sequences, specifically, the six binary strings to be used would be the three pairs of binary strings corresponding to the three nucleotides of the DNA (or messenger RNA) strand that form the codon for each amino acid. The genetic code is redundant and most of the amino acids correspond to more than one codon of three nucleotide bases, in fact 61 of the possible 64 combinations represented by a six bit binary number provide the code for an amino acid (the remaining three are stop codons).

One of the advantages in using this representation is that there are many searches that involve combining information from proteins with information from nucleotide data bases. In such cases it is current practice to translate the nucleotide information into amino acid format for comparison with the protein data. Since the reading frame (where to start translating the set of three nucleotides forming the codon) can be in any of three starting places ('frame shifts') on the sense strand or on any of three places on the complementary strand, there are six sets of amino acid sequences typically created from the nucleotide sequences for comparison with the protein sequences. With this method of representation, the six binary strings immediately provide one of these six representations and two successive left shifts by one bit location provide two more of the six needed. Also, since the complementary strand is directly available from the binary strings of the sensing strand, the same process provides the remaining three amino acid representations.

For sequence alignment (either local or global) of amino acids, it is rare to find long sequences that match exactly and there are scoring matrices for various mismatches. Certain mismatches do not change the essential character or function of the resulting protein domain and are considered 'accepted' and receive a higher score in standard scoring tables created for this purpose such as PAM or BLOSUM. In performing sequence alignments of amino acids, there is a high premium on identification of quick means to characterize 'candidate' alignments that might have reasonable scores using the various scoring matrices. The proposed representation as three sets of two binary strings lends itself ideally to this need.

Another advantage in using 6 binary strings to represent an amino acid sequence is found in the property that most of the amino acids are already determined by the first two nucleotides of the three-membered codon. Hence, only the first 4 of the six binary strings would have to be searched to find strong candidate matches for alignment. Furthermore, when this fails to provide a unique identification by means of the first two parts of the codon (4 binary strings), there is very often (but not always) a strong relationship between the different amino acids that could result; e.g., (1) phenylalinine and leucine both start with AA in the DNA codon (or UU in the corresponding mRNA codon), both have side chains which are chemically non-polar, and a mismatch only results in a neutral score (BLOSUM62) or even a favorable score (PAM250), so no serious 'error' occurs by using the first two letters (4 digital strings) as an initial check for alignment, (2) similarly the codons for aspartic acid and glutamic acid both start with the letters GA, both have acidic side chains and a positive score assigned by both BLOSUM and PAM for a mismatch.

Since there are several codons that result in the same amino acid, there may be an ambiguity as to which form to use. In some cases (as when the mRNA sequence that generated the protein is known, or when the protein is obtained by translation from a nucleotide sequence), the exact codon to use is available. It is also known that certain species and/or specific tissues favor particular codons to represent the amino acids. If no other information is available, there exist statistical studies which have established the relative frequency of the use of one specific codon instead of another. Hence, in the absence of any other data, the most frequently observed codon could be used for a particular amino acid, or, alternately, a pseudo-random choice could be made that is statistically in accordance with the ratios of the observed frequencies of codons that generate each amino acid. The user has the flexibility to select whatever encoding is most appropriate for the particular search.

When there is a mismatch at any position, current practice uses a scoring matrix (such as PAM or BLOSUM) to assign a value to the mismatch for each amino acid against each other amino acid. The table is accessed by the pair of amino acids that mismatch and these provide essentially the row and column of the 20×20 table to locate the particular value or score associated with that pairing. This same method is directly available for a mismatch of the query and the target by using the six-bit string of the query and the six-bit string of the target as the row and column locators in exactly the same way as the amino acid names are used in current practice. However, the proposed method of encoding opens up the possibility of a more refined scoring method that takes into account not only the amino acid mismatch but the nature of one or both of the codons that created these amino acids. This might be used when there is actual knowledge of the codons from mRNA data or by translation from a nucleotide sequence. If such data is lacking, the current 'standard' tabular entries of a PAM or BLOSUM matrix could, of course, still be used. The augmented table would now be a 32×32 table corresponding to the two 6-bit representations. The general approach to scoring which makes use of the unique encoding of this invention is provided in more detail in Example 3 below.

In searches of protein data bases it is common practice to use very short search queries of only 2 or 3 amino acids in length ("k-tuples") created from the parts of the query string to find initial identical matches that are subsequently extended by algorithms such as dynamic programming to find the optimal overall match. With the representation proposed, these k-tuples are simply an array of 2×6 (or 3×6) with the entries all either zero or one. The target amino acid sequence of length N is an N×6 array also with entries that are either zero or one. To located the desired identities for the initial k-tuple search, the 2×6 (or 3×6) test matrix is indexed along the length of the target sequence and at each index position there is a matrix addition performed using again the exclusive or form of addition. An identity is found if and only if every entry of the 2×6 (or 3×6) matrix is exactly zero. As noted previously, such array operations with arrays consisting solely of ones and zeros could be further accelerated by incorporating a custom module (chip) designed for this specific purpose.

Gaps can be introduced in the same manner as presently done. The digital strings are separated at the gap location and form two strings at a defined index separation. For strings that are already in digital form, this amounts to no more than a simple shift of the second string with respect to the first. The amount of shift is determined by the nature of the gap to be introduced and is generally part of the algorithm used to search for alignments. Typically, the algorithm(s) assign a penalty in the scoring to opening of the gap plus an additional penalty for each extension, e.g. Affine Smith-Waterman, for example.

EXAMPLE 3

Biomolecular Alignments

A software system for sequence alignment was developed based on 1) the functional decomposition of the initial search string into a set of n bit-vectors that function as feature-vectors in an n-dimensional space, 2) the alignment of probe feature-vectors with text feature vectors using a fast bit-vector algorithm (Myers, G., Journal of the ACM 46(3), 1999), and (3) the scoring of the resultant alignments using a probabilistic distance metric based on the feature space. (see, for example, FIG. 1).

Because we decomposed probe sequences into collections of feature-based bit-vectors, it was possible to design searches that are both feature-specific and very fast.

The Functional Decomposition of the Search String into a Sieve

Every binary string in a sieve is a measurement of a feature. The creation of a sieve maps the original symbol sequence into a collection of binary sequences, each exemplifying a different trait of the molecule represented by the sequence.

A sieve is a set of several different binary strings, each derived from a single sequence by some deterministic process. The number of strings in the sieve is the sieve's size. Every string in a sieve is the measurement of a feature. Thus, a given sieve depcts a number of features equal to the number of strings in the sieve (represented as n in the formula listed below).

In this application, a sieve is a collection of bit-vectors derived from the features of the amino acid residues in a single amino acid sequence. Each vector in the sieve is designed to measure the presence or absence of a trait or feature.

Given a sequence of symbols $$S=\{s_1, s_2, \ldots, s_m\},$$

a sieve is defined to be a set of bit-vectors, $$V=\{v_1, v_2, \ldots, v_n\},$$

where $$v_i = f_i(S)$$

and $f_i$ is a well-defined function mapping each symbol or set of symbols in S to either a 0 or 1 such that if the feature is present or true for the symbol(s) at a given position i in a sequence, then the $i^{th}$ position in the bit-vector is set to one (1), otherwise it is set to zero (0).

In this implementation, each vector in V has the length of the original sequence, S.

In computational biology, where sequence symbols correspond to either monomers or residues, there are a wide variety of features that can be ascribed to each symbol ranging from simple features like size, polarity, and charge to more esoteric elements like the frequency of appearance in globular proteins, the likelihood of binding to a metal ion, the set of related codons (if the original sequence is an amino acid sequence) or the set of related amino acids (if the original sequence is a nucleic acid sequence), A symbol can also be considered in terms of its neighbors—whether the current symbol is embedded in a hydrophobic region, whether the symbol appears to be between domains, or whether the symbol appears with certain regularity or pattern. We can use features that are context-free or we can use to features that are context-dependent.

Moreover, any set of features can be used; there is no restriction on the feature-vectors that can construct the sieve except efficiency. However, the more orthogonal the feature-vectors, the more efficient a sieving strategy will be.

In practice multiple sieves were explored; so-called structure sieves and BLOSUM sieves as described below.

Structure Sieves

The physico-chemical sieves are based on observations of amino acid structural and chemical properties: size, polarity, rate of post-translational modification, frequency of appearance in beta sheets, and frequency of appearance in alpha coils.

There were five features and both the probe and database sequences were decoded into 5 different bit-vectors.

To handle preprocessing efficiently, a table of processed entries was constructed. The final table was of size 2*5—the number of different elements in the preprocessed text (0,1) and the number of features (5).

BLOSUM Sieves

This scoring sieve was based on the observation that types of amino acids tended to cluster in terms of frequency of substitution with one another. This holds true in both BLOSUM and PAM. Moreover, the clusters stayed nearly identical over evolutionary time—e.g., from BLOSUM 10 to BLOSUM 100.

These were the groups of amino acids selected:
sulfhydryl: C
small hydrophilic: S, T, P, A and G
acid, acidamide and hydrophilic: N, D, E and Q
basic: H, R and K
small hydrophobic: M, I, L and V
aromatic: F, Y and W The individual alphabetic characters above correspond to individual amino acids.

The sieves were built based on degrees of clustering. The concentration was on substitution pairs, so that the probe was indexed and the database sequence was preprocessed so that each letter in the sequence was scored in 6 different ways, one for each degree of clustering. At the top level, only pairs with pairwise substitution scores greater than 6 were awarded a "match" or score of 1, at the bottom level, all pairs with substitution scores greater than −1 were awarded a match.

For efficiency, a lookup table of size 24*6 was used for preprocessing the text. Here, each letter in the text (there are 24-23 for the extended set of amino acids and 1 for single-residue gaps) and each of the six cluster levels are represented.

Sieve Storage

Note that the decomposition of sequences could be run for entire data sets in batch so that the data is already preprocessed when an alignment query is invoked. In practice, it was most efficient to process sequences into datasets and store them.

Alignment with Sieves and a Bit-Vector Algorithm

Given a query sequence, Q, and a text sequence, T, define the related sieves as $$V_q = (v_{q1}, v_{q2}, \ldots, v_{qn})$$

and $$V_t = (v_{t1}, v_{t2}, \ldots, v_{tm})$$

A sieving strategy matches bit-vector i from the sieve for the query, $v_{qi}$ with $v_{ti}$ for the text and performs an approximate match. Any bit-vector matching algorithm can be used.

If the number of differences for the match is under some difference threshold, say k, we then move on to the next element in the sieves. If the match fails, however, no further matches are attempted.

Sieving or filtering in this way can be done judiciously or arbitrarily. The best strategy presents the hardest to match sieve vectors first, the worst presents the easiest to match first. The best strategy uses bit-vectors that measure independent features, the worst strategy uses bit-vectors that measure the same features redundantly.

For optimal bit-vector alignment the method presented by Myers is used (see references). The advantage of this method is that it is very fast, the disadvantage is that it performs approximate string matching without incorporating edit distance information, using simple 0's and 1's to indicate a match or mismatch.

The preprocessing of probes for Myers' algorithm is based on Hyyro and Navarro, 2003.

Alignment Scores

The output of the Myers alignment is a difference value k for each of the bit-vector alignments. While informative, a more rigorous score was invoked in practice.

The log probability of a sequence alignment given two bit-vectors taken from the same pool of sequences is estimated from that pool by measuring the fraction of all pairs including 0 as $q_0$, the fraction of all pairs including 1 as $q_1$ and the fraction of all pairs including both 0 and 1 as $p_{01}$. The result is $$S = \Sigma_i s(0_i, 1_i)$$

where $$s(0,1) = \log(p_{01}/q_0 q_1)$$

Given an unbiased measure for s(0,1) for each feature in the sieve, we can score each alignment in the standard way (c.f. Needleman-Wunsch, J. Mol. Biol. 1970, and Smith-Waterman, J. Mol. Biol. 1981). Given orthogonal measures, these log probabilities can be accurately summed across sieves and attain the corresponding soundness of significance that is enjoyed by SSEARCH. Note that failure to obtain orthogonality biases the probability measure.

In addition to sieve probability scores, an additional measure is called "confirmation". These are the number of alignments found that have an end point close to or near the highest scoring alignment. There are internal confirmations and external confirmations Internal confirmations are generated during the same alignment run and correspond to finding more than one good alignment for the same query and text sieve vectors. External confirmations are ascribed to good alignments between query and text with similar ending locations but from different sieve vectors.

Performance Summary

The alignment strategy described here was concretized by coding in Java and copyrighted by ELORET. Benchmarking was done against a faithful implementation of the Smith-Waterman algorithm. Benchmarking was accomplished using data from the Structural Classification of Proteins (SCOP) database supplied to the public by Steven Brenner's lab at University of California, Berkeley.

The software implementation had time complexity comparable to the speed efficiency of the Myers' algorithm. The software successfully identified and ordered similar sequences with accuracy comparable to the Smith-Waterman approach.

EXAMPLE 4

Lexicographic Sequences

The present US ASCII standard consists of the lower case letters a-z, the upper case letters A-Z, the numbers 0-9, various punctuation marks and various control characters (such as shift or space). There are 128 such 'plain text' elements and consequently 7 bits would be required to fully distinguish each of these lexicographic characters. However, by convention, these are represented as a byte of 8 binary bits. From the general explanation at the top, any such sequence could be represented as 7 (or 8) binary strings of length equal to the length of the lexicographic sequence. The pattern to be found is also of the ASCII form and can be represented by 7 (or 8) binary strings of length equal to the length of the query. The method previously described now applies where matching any one of the binary strings of the query sequence with its opposite number in the target sequence is a necessary condition and matching all 7 (or 8) represents a sufficient condition.

Flexible, focused approximate matching can be achieved by the techniques described in Example 3. As previously noted, the advantage of the novel method increases with the length of the query sequence to be matched since each one of the binary strings of the decomposition of that query serves to narrow the search domain by a factor proportional to ½ to the Mth power where M is the length of the query sequence.

EXAMPLE 5

Speech Understanding

The practice is to reduce speech to a finite specific set of sounds called phonemes which are characterized by a letter of the phonetic alphabet. These now can be considered to be the elements of a sequence and the time series of the sounds represents the index positions of the members of the sequence. If each of the phonetic elements is encoded as a set of parallel binary strings and a dictionary of sounds is constructed in the same manner, the search process would be exactly the same kind of search as done by a sequence against a database for amino acid or DNA sequences. That is, a necessary condition for a match is that each of the binary strings of the query sequence matches (or scores high) against the corresponding binary string of the target sequence. A 'hit' only indicates a candidate find and to confirm a match, the 'hit' must occur at the same index position for each of the remaining binary strings. The match only needs to be checked at the same index position and not along the entire length of the sequence (which could be long) thus narrowing the search domain. If parallel processing capability is available, then all the binary strings of the encoded query can be tested at the same time against the corresponding binary strings of the target sequence. The search and scoring method of Example 3 may also be adapted here to provide for flexible, feature-dependent scoring.

EXAMPLE 6

Voice Prints and Voice Identification

There are individual variations in speech patterns such as differences in duration, frequency, intonation, etc. These are frequently characterized in terms of variations in vowel sounds (formant patterns) and the transitions between the formants. Since these variations are finite in number, a database can be created which includes these individual variations. Since the set of variations is finite, it can be represented by a set of binary strings. Then, for a particular speaker, the individual variations can be used to create a custom test sequence with which to search the database of previously stored sequences that include samples of individual variations in order to find a best match. Depending on how solid a match is found, a probability of identification of a particular speaker can be determined. This might be used, for example, to determine if a speech is indeed being spoken by a specific individual. A more common usage is for speaker identification to be used for entry into secure areas. In this case, the database is constructed as a library of sequences where the spoken sounds of all cleared personnel are in the library file and specific strings and phrases have been selected to best distinguish the voiceprints of individuals seeking access. Both the library of stored sequences as well as the test or query sequence must be encoded as a set of binary strings in accordance with the general method described.

EXAMPLE 7

Fingerprint Validation and Identification

Given an input and a set of many different stored fingerprints, the problem of identification is to compare the input fingerprint with a set of stored fingerprints and decide if the input fingerprint matches one of the stored prints.

Usually the problem is broken down into two parts—1) the extraction of fingerprint feature data from raw images and 2) the comparative matching of input features and stored feature sets. Only the second problem, matching, is addressed.

The general process for fingerprint matching using the current invention is as follows:

Estimate the translation and rotation parameters between input and template features and convert into the same frame of reference using extant methods.

Decompose the input fingerprint features into an input sieve and decompose the set of stored fingerprint feature sets into stored sieves.

Match the resulting sieves using a fast bit-vector approximate string matching algorithm.

Bringing input and template features into registration, as described in Step 1, is a problem that has been addressed and solved in the literature. The novel idea is to decompose fingerprint feature strings into related bit-vectors and then use a fast bit-vector approximate string matching algorithm.

Sieves in Fingerprint Analysis

Sieves can be created from a number of different kinds of extracted features. The features extracted from fingerprint images are usually minutia and the following method uses minutia as its primary example. However, the method below will work for other feature sets—including Gabor flow.

Minutiae are, at base, dependent on ridge bifurcation and/or ridge ending information. The simplest of the minutiae-based representations are comprised of a list of such points defined by their spatial coordinates with respect to a fixed image-centric system. Typically these minimal representations are enhanced by tagging minutia (or minutiae tuples) with additional features including the location and rotation of the minutia or the number of ridges between minutiae or the quality/likelihood of the minutia given the initial data.

In the case of minutiae, breaking down the extracted feature string into bit-vectors can be quite novel. One method is to pad out an appropriately sized two-dimensional matrix with 0's building a two-dimensional template on which to place location and rotation data. The location of various types of minutiae are incorporated as 1's. The resulting matrix can then be reduced to a one-dimensional sequence.

One may construct such matrices to treat the locations of both simple and complex features—from basic minutiae like ridge bifurcation and ridge ending to more complex features like arches, whorls, loops, deltas and cores.

Storage

Storage of fingerprint sieves speeds up the matching process. Therefore, databases used for efficient fingerprint identification will contain sieves for each set of extracted fingerprint features.

Performance Estimation

The fingerprint validation and identification problems both devolve to the solution of fingerprint matching between input and template. When validating, the problem involves matching one input and one template. When determining identity, the problem involves matching one input to many templates. In the first case, one extracts the input features once and matches once. In the second case, one extracts the features once but then checks through a set of possible templates and matches. Therefore, the novel method, which improves match speed but does not effect extraction speed, is most useful for fingerprint identification. In that arena, standard match algorithms have an average time-complexity of O(mn), where m is the average number of minutia extracted per fingerprint and n is the total number of minutia compared against a database of fingerprint data. Since sieves can exploit 0(n) bit-vector algorithms and since m is usually greater than 100, our method is estimated to be more than 100 times faster than the current standard in fingerprint identification.

EXAMPLE 8

Signal Analysis

For the case of signal analysis (electromagnetic, optical, acoustic, seismic), the information content may appear to be continuous rather than in the form of a discrete sequence with a finite number of elements at each index position. However, any time series can be chopped into a finite number of discrete sub-sets and in many applications, comparatively short time-varying signals can be classified into a finite number of quite specific patterns of interest to analysts. Common examples include radar or sonar returns which may indicate targets. Also, there are unique seismic patterns that may indicate precursors of earthquake or volcanic activity. Similarly, in oil exploration, the seismic returns induced by controlled explosions contain patterns that may indicate dome formations Once the information is placed in the form of one or more sequences in which each index position can assume a finite number of variations, the general method described in Example 3 can be applied to search these sequences for specific patterns of interest by encoding the query pattern as a set of binary strings and encoding the target sequences in the same manner. The scoring of approximate matches can be customized to emphasize the specific features of importance for this application.

EXAMPLE 9

Image Patterns

The invention can be applied to an entirely different and important class of applications that contain patterns which are not normally considered to be sequential. Consider, for example, an image of any type such as a photograph, a fingerprint, an x-ray, CAT scan, MRI image, or an image on a TV screen. On the one hand this is a fixed, static display and not a sequence. However, for a TV image, there is actually a sweep across the rows of the screen and at each pixel location (index) there is a dot (or superposition of dots for color, hue, etc.). Any static image can be scanned in some order (say left to right starting with the top row and then the next row, etc.) and the result of the scan at each location then represents an element of a sequence corresponding to the content at that pixel position and the length of the sequence is the total number of pixels scanned. In the simplest case, each pixel would either have a black dot or none and a single binary string of 1's and 0's would be sufficient to encode the result of the scan. This is consistent with the prior formulation of the minimum number of binary strings needed since, in this example, the number of distinct elements=2 and log2=1 for base 2 logarithms. As considerations such as color, hue, intensity, etc. are added to the content of each location of the scan, the number of binary strings needed to represent a decomposition of the resulting sequence would increase accordingly. The same general search method described to locate DNA or amino acid patterns could be applied directly to search for a particular image at any location on the scanned image or, to search for a close match in accordance with a particular scoring schema.

In many pattern matching issues involving images, there are specific features of importance to a specialist other than the raw sequential recording of pixels resulting from a sweep of the image. For example, in fingerprint identification or authentication, it is common practice to concentrate on particular properties of the ridges called minutiae such as ridge terminations or bifurcations (as well as others). The presence or absence of such minutiae as well as their relative locations form the basis for the identification/authentication process. Modern recording of fingerprints use 500 dpi scanners (in some cases 800 dpi scanners) to obtain an electronic image of the print and there are existing automated methods to identify and extract the minutiae. In order to employ the method of this patent, the space would be divided into regions of 15×15 (or 20×20) pixels which would result in sequence of approximately 600-700 such regions. Each member of the sequence (representing one of the regions) would have properties such as, 'no minutiae', 'ridge termination', 'ridge bifurcation', etc. Current practice indicates that there would be no more than 8 such features or properties and consequently this would correspond to decomposition of the sequence into 4 binary strings of length equal to the number of regions (approximately 600-700). The search for a match would then proceed exactly as in the cases illustrated above. Scoring of approximate matches would be based on the importance of mismatches as defined by experts in this field.

EXAMPLE 10

Game Playing

Many games such as chess, for example, consist of a sequence of moves or, equivalently, a sequence of states. In the case of chess, the states would be the positions of all the pieces at each stage of the game. The possible number of moves (or number of changes of state) at any given turn may be quite large but still finite. By encoding the move sequence (or the current state at each step) as a set of binary strings sufficient to encompass all the available moves at that turn, the method described can be used to search a database of prior games (or states) and recover information such as the outcome resulting from various subsequent choices, previously established evaluations of the position, historical data, etc.

EXAMPLE 11

Law Enforcement

Several of the disciplines previously described would have immediate application in the area of law enforcement. These include (but are not limited to) searches of fingerprint databases, voiceprint databases and DNA testing. An additional approach would be to establish a database of physical characteristics to be used as an aid in identification. The number of characteristics selected for inclusion in such a database would determine the length of the sequence and the maximum number of variations of each characteristic would determine the number of parallel binary strings in the decomposition. Once the query and the target are in the form of this invention, the process of finding a matching pattern (or the closest patterns if an exact match is not required) would proceed in the manner described previously for DNA or amino acid sequences. Still another possible application to law enforcement would be to establish a database of the modus operandi of known criminals and their methods of carrying out their crimes. The novel method can then search such a database with a pattern of a new crime to find exact matches (or a listing of closest matches) with prior patterns in the database.

EXAMPLE 12

Medical Diagnosis and Health Care

Many of the potential applications have been incorporated into prior sections such as those dealing with image patterns α-rays, MRI, CAT scan, etc.). In medical imaging, there are characteristic patterns that are used by experts for diagnostic purposes. The finite number of specific characteristics on a medical image used by skilled diagnosticians as well as their conclusions can be encoded in a database in the particular form required by this invention. Then a patient image can be encoded and the database searched for a pattern match (or a list of close partial matches) to assist a less-specialized physician in drawing preliminary conclusions from the data.

An additional aspect of medical diagnostics and healthcare concerns the area of pharmacogenetics wherein the differences in the response of individuals to therapeutic treatments (e.g., drugs) can be caused by variations at the DNA level (Nebert et al. Trends in Biotechnology. Volume 19, Issue 12, 1 Dec. 2001, Pages 519-523). Nebert et al reported that "inter-individual differences are often more than tenfold; a 'slow metabolizer' or 'low-responsive' individual might therefore require ten times less than the recommended dose of a drug than a 'rapid metabolizer' or 'high-responsive' person, and the slow metabolizer is often more likely to experience drug toxicity than a rapid metabolizer." By decomposing the information content of the target sequence and the query pattern into a set of simpler representations to enable the search process to make maximum use of computational and logical steps, this invention has a potential to help physicians use DNA-based tests to aid in decision-making with respect to the most appropriate drug and dosage given to each patient.

EXAMPLE 13

Equipment Maintenance

Parameters such as temperatures, pressures, strains, level readings of gauges, etc. are measured and recorded at regular time intervals to measure the condition of complex equipment such as aircraft, nuclear plants, power stations, etc. This time series of measurements can be regarded as a sequence where the index of the sequence is the particular time reading and the features or elements at any index position describe the state in terms of the values (or ranges) of the critical parameters. Reference sequences based on prior experience can be compared to the pattern formed from a current sequence to determine potential failures of subsystems or to indicate excessive wear. Portions of the system requiring replacement or maintenance can be identified from the comparison with the reference sequence(s). The sequence formed from the time series of measurements as well as the reference sequence(s) can be encoded as a set of binary strings and the search for a match would be conducted in the same manner as described in detail for other applications. The number of parallel binary strings needed for such an application is determined by the number of states used to describe the set of measurements.

REFERENCES

Each of the following articles is incorporated herein by reference.

Myers, G., 'A fast bit-vector algorithm for approximate string matching based on dynamic programming,' Journal of the ACM, 46(3): 305-415, 1999.

Mount, David W., 'Bioinformatics Sequence and Genome Analysis,' Cold Sprint Harbor Laboratory Press, Cold Spring Harbor, N.Y., 2001.

Maltoni, D., Maio, D., Jain, A. K., Prabhakar, S., 'Handbook of Fingerprint Recognition', Springer-Verlag, New York, 2003.

Needleman, S. B. and Wunsch C. D., 'A General Method applicable to the search for similarities in the amino acid sequence of two proteins,' J. Mol. Biol. 48: 443-453 1970

Waterman, M. S., Ed. Mathematical analysis of Molecular Sequences (special issue) Bull. Math. Biol. Pergamon Press, New York 1989.

Smith T. F., and Waterman, M. S., 'Identification of Common Molecular Subsequences,' J. Mol. Biol. 147, 195-197, 1981.

Smith, T. F., and Waterman, M. S., 'Comparison of biosequences,' Adv. Appl. Math. 2482-489,1981

Champod, 'Fingerprints and Other Ridge Skin Impressions,' CRC Press, Atlanta, Ga., Navarro, G., 'A Guided Tour to Approximate String Matching,' ACM Computing Surveys, 2000.

Although the invention has been described with reference to the above examples, it will be understood that modifications and variations are encompassed within the spirit and scope of the invention. Accordingly, the invention is limited only by the following claims.

What is claimed is:

1. A method of comparing sequential data using a computer system, comprising:
  (a) providing to a first storage device a target sequence having at least a first binary string n bits in length and a second binary string n bits in length, the second binary string aligned with the first binary string to form n groups of aligned bits, each group of aligned bits including one bit from the first string and the corresponding bit from the second string, each group of aligned bits defining a component member of the target sequence;
  (b) providing to a second storage device a query sequence having at least a first binary string m bits in length ($m \leq n$) and a second binary string m bits in length, the second binary string aligned with the first binary string to form m groups of aligned bits, each group of aligned bits including one bit from the first string and the corresponding bit from the second string, each group of aligned bits defining a component member of the query sequence;
  (c) comparing the m bits contained in the first binary string of the query sequence against the n bits contained in the first binary string of the target sequence to determine first matches between the first binary string of the query sequence and the first binary string of the target sequence, each first match, if any, defining an m-bit segment having a match position m bits in length in the first binary string of the target sequence, and, for each first match, if any, associating the match position in the first binary string of the target sequence to the corresponding m-bit segment of the second binary string of the target sequence;
  (d) for each first match, if any, comparing the m bits contained in the second binary string of the query sequence against m-bit segments of the second binary string of the target sequence corresponding to such first match to determine second matches, if any, between the target and query sequences;
  (e) generating an indication of matches, if any, between one or more of the binary strings of the target sequence and the binary strings of the query sequence and outputting said indication to a user interface.

2. The method of claim 1, further comprising:
  (a) for each second match, if any, associating the match position in the second binary string of the target sequence to corresponding m-bit segments of a third binary string of the target sequence; and
  (b) comparing the m bits contained in a third binary string of the query sequence against one or more of the m-bit segments of the third binary string of the target sequence to determine third matches, if any, between the target and query sequences.

3. The method of claim 1, wherein said indication of matches includes information identifying at least one of the first matches.

4. The method of claim 1, wherein said indication of matches includes information identifying at least one of the first matches and at least one of the second matches.

5. The method of claim 1, wherein the first and second storage devices include random access memory locations of said computer system.

6. The method of claim 1, wherein said user interface is connected to said computer system through a communications interface.

7. The method of claim 1, wherein said component members of said target and query sequences represent component members of amino acid sequences.

8. The method of claim 1, wherein said component members of said target and query sequences represent component members of nucleotide sequences.

9. The method of claim 1, wherein the method further comprises the step of terminating all subsequent comparison steps if no first match is found, generating an indication of no first match being found and outputting said indication to a user interface.

10. The method of claim 1, wherein the method comprises the step of ordering said m-bit segments of the second binary string of the target sequence into an auxiliary binary string of length N*m (where N equals said number of first matches) and comparing the m bits contained in the second binary string of the query sequence against the auxiliary binary string to determine second matches, if any, between the target and query sequences.

11. The method of claim 1, further comprising the step of comparing the m bits contained in the first binary string of the query sequence against the n bits contained in the first binary string of the target sequence to determine partial matches between the first binary string of the query sequence and the first binary string of the target sequence.

12. The method of claim 1, wherein said first matches, if any, include partial matches determined using a subset of the m bits contained in the first binary string of the query sequence.

13. The method of claim 1, wherein said second matches, if any, include partial matches determined using a subset of the m bits contained in the second binary string of the query sequence.

14. An apparatus for comparing sequential data, comprising:
  (a) a first digital storage device configured to store a target sequence having at least a first binary string n bits in length and a second binary string n bits in length, the second binary string aligned with the first binary string to form n groups of aligned bits, each group of aligned bits including one bit from the first string and the corresponding bit from the second string, each group of aligned bits defining a component member of the target sequence;

(b) a second digital storage device configured to store a query sequence having at least a first binary string m bits in length ($m \leq n$) and a second binary string m bits in length, the second binary string aligned with the first binary string to form m groups of aligned bits, each group of aligned bits including one bit from the first string and the corresponding bit from the second string, each group of aligned bits defining a component member of the query sequence;

(c) first digital processor configured to compare the m bits contained in the first binary string of the query sequence against the n bits contained in the first binary string of the target sequence to determine first matches between the first binary string of the query sequence and the first binary string of the target sequence, each first match, if any, defining an m-bit segment having a match position m bits in length in the first binary string of the target sequence;

(d) a second digital processor configured to compare the m bits contained in the second binary string of the query sequence against each m-bit segments of the second binary string of the target sequence corresponding to each first match to determine second matches, if any, between the target and query sequences;

(e) a third digital processor configured to generate an indication of matches, if any, between one or more of the binary strings of the target sequence and the binary strings of the query sequence and to output said indication to a user interface.

15. The apparatus of claim 14, wherein the first and second digital storage devices include random access memory locations of a computer system.

16. The apparatus of claim 14, wherein one or more of the first, second and third digital processors is a field programmable gate array.

17. The apparatus of claim 14, wherein one or more of the first, second and third digital processors is an application specific integrated circuit.

18. The apparatus of claim 14, further comprising a fourth digital processor configured to generate a score for one or more of said first and second matches, if any, based on the number of identical bits appearing in each said match.

* * * * *

UNITED STATES PATENT AND TRADEMARK OFFICE
CERTIFICATE OF CORRECTION

PATENT NO. : 8,280,640 B2
APPLICATION NO. : 10/916370
DATED : October 2, 2012
INVENTOR(S) : Eugene Levin et al.

It is certified that error appears in the above-identified patent and that said Letters Patent is hereby corrected as shown below:

In the Claims

Column 45, Line 10, Claim 14, change "first digital processor" to– "a first digital processor"

Signed and Sealed this
Twenty-seventh Day of May, 2014

Michelle K. Lee
*Deputy Director of the United States Patent and Trademark Office*

SEQUENCE LISTING

```
<160> NUMBER OF SEQ ID NOS: 7

<210> SEQ ID NO 1
<211> LENGTH: 34
<212> TYPE: DNA
<213> ORGANISM: Artificial sequence
<220> FEATURE:
<223> OTHER INFORMATION: Target sequence

<400> SEQUENCE: 1
gataccttag gaactgaaaa aggattcagg actg                                  34

<210> SEQ ID NO 2
<211> LENGTH: 840
```

```
<212> TYPE: DNA
<213> ORGANISM: Homo sapiens

<400> SEQUENCE: 2
gtgaaggtaa gtacctacac caaaaactgt agccagaaaa ggcttgttat cctaccttta    60
gacaggtaga agattgtggg agatgggcgc gagaaactcc gtcttgagag ggaaaaaagc   120
agacgaatta gaaaaagtta ggttacggcc cggcggaaag aaaaagtaca ggttaaaaca   180
tattgtgtgg gcagcgaatg aattggataa attcggattg gcagagagcc tgttggagtc   240
aaaagaaggt tgccaaaaga ttctcagagt tttagatcca ttagtaccaa cagggtcaga   300
aaatttaaaa agctttttta ataccgtctg cgtcatttgg tgcttgcacg cagaagagaa   360
agtgaaagat actgaggaag caaagaaact agcacagaga catctagtgg cagaaactgg   420
aactgcagag aaaatgccaa atacaagtag accaacagca ccacctagtg ggaaaagagg   480
aaactacccc gtgcaacaag cgggtggcaa ctatgtccat gtgccactga gcccccgaac   540
tctaaatgca tgggtaaaat tagtggagga aaagaagttc ggggcagaag tagtgccagg   600
atttcaggca ctctcagaag gctgcacgcc ctatgatatt aatcaaatgc ttaattgtgt   660
gggcgatcac caagcagcta tgcaaataat cagagagatt attaatgaag aagcagcaga   720
ctgggattcg cagcacccaa taccaggccc cttaccagca ggacagctca gagacccaag   780
agggtctgac atagcaggaa caacaagcac agtagatgaa cagatccagt ggatgtatag   840

<210> SEQ ID NO 3
<211> LENGTH: 34
<212> TYPE: DNA
<213> ORGANISM: Artificial sequence
<220> FEATURE:
<223> OTHER INFORMATION: Complementary sequence of SEQ ID NO:1

<400> SEQUENCE: 3
ctatggaatc cttgactttt tcctaagtcc tgac                                34

<210> SEQ ID NO 4
<211> LENGTH: 36
<212> TYPE: DNA
<213> ORGANISM: Yeast

<400> SEQUENCE: 4
gcagcgcacg acagctgtgc tatcccggcg agcccg                              36

<210> SEQ ID NO 5
<211> LENGTH: 36
<212> TYPE: DNA
<213> ORGANISM: Artificial sequence
<220> FEATURE:
<223> OTHER INFORMATION: Mutation sequence of SEQ ID NO:4

<400> SEQUENCE: 5
gcagcgcacg acagctgtgc tatcccggcg accccg                              36

<210> SEQ ID NO 6
<211> LENGTH: 12
<212> TYPE: DNA
<213> ORGANISM: Artificial sequence
<220> FEATURE:
<223> OTHER INFORMATION: Common Region of Identity sequence

<400> SEQUENCE: 6
aggtactcga ct                                                        12
```

-continued

```
<210> SEQ ID NO 7
<211> LENGTH: 13
<212> TYPE: DNA
<213> ORGANISM: Artificial sequence
<220> FEATURE:
<223> OTHER INFORMATION: Common Region of Identity sequence

<400> SEQUENCE: 7
gcctatgact cga                                                      13
```